US012708287B2

(12) United States Patent
Kuller

(10) Patent No.: US 12,708,287 B2
(45) Date of Patent: Aug. 18, 2026

(54) BREATH VOLUME MONITORING SYSTEMS AND METHODS

(71) Applicant: MyAir, Inc., Boston, MA (US)

(72) Inventor: David T. Kuller, Milan (IT)

(73) Assignee: MyAir, Inc., Boston, MA (US)

( * ) Notice: Subject to any disclaimer, the term of this patent is extended or adjusted under 35 U.S.C. 154(b) by 1096 days.

(21) Appl. No.: 17/724,885

(22) Filed: Apr. 20, 2022

(65) Prior Publication Data

US 2022/0338755 A1 Oct. 27, 2022

Related U.S. Application Data

(60) Provisional application No. 63/201,275, filed on Apr. 21, 2021.

(51) Int. Cl.

*A61B 5/091* (2006.01)
*A61B 5/00* (2006.01)
*A61B 5/08* (2006.01)
*A61B 5/113* (2006.01)

(52) U.S. Cl.

CPC ............ *A61B 5/091* (2013.01); *A61B 5/0816* (2013.01); *A61B 5/1135* (2013.01); *A61B 5/6823* (2013.01); *A61B 5/7246* (2013.01); *A61B 5/7425* (2013.01); *A61B 5/743* (2013.01)

(58) Field of Classification Search

None

See application file for complete search history.

(56) References Cited

U.S. PATENT DOCUMENTS

| | | | |
|---|---|---|---|
| 4,597,394 | A | 7/1986 | Sackner |
| 4,715,235 | A | 12/1987 | Fukui et al. |
| 4,807,640 | A | 2/1989 | Watson et al. |
| 4,815,473 | A | 3/1989 | Watson et al. |
| 4,834,109 | A | 5/1989 | Watson |
| 5,076,281 | A | 12/1991 | Gavish |
| 5,159,935 | A | 11/1992 | Sackner et al. |
| 9,504,410 | B2 | 11/2016 | Gal |

(Continued)

FOREIGN PATENT DOCUMENTS

| | | | |
|---|---|---|---|
| EP | 3151748 | A1 | 4/2017 |
| WO | WO-2005067796 | A1 | 7/2005 |

(Continued)

OTHER PUBLICATIONS

International Preliminary Report on Patentability in International Application Serial No. PCT/US2022/025489, mailed Nov. 2, 2023, 9 pages. (Year: 2023).*

(Continued)

*Primary Examiner* — Meredith Weare

(74) *Attorney, Agent, or Firm* — Schwegman Lundberg & Woessner, P.A.

(57) ABSTRACT

Monitoring systems and methods for measuring one or more physiological parameters of an individual. More particularly, systems and methods for monitoring one or more parameters or other data relating to the breath volume of an individual, determining various breath characteristics or indicators based on breath volume data, and providing a meaningful display of the breath characteristics or indicators for easy and quick identification and/or diagnosis of breathing-related or other health conditions.

14 Claims, 24 Drawing Sheets

(56) References Cited

U.S. PATENT DOCUMENTS

| | | | | |
|---|---|---|---|---|
| 10,123,724 | B2 | 11/2018 | Kuller | |
| 10,194,835 | B2 | 2/2019 | Beyar et al. | |
| 2002/0032386 | A1 | 3/2002 | Sackner et al. | |
| 2002/0123692 | A1 | 9/2002 | Pail | |
| 2003/0187341 | A1 | 10/2003 | Sackner et al. | |
| 2004/0143194 | A1 | 7/2004 | Kihara et al. | |
| 2005/0119586 | A1 | 6/2005 | Coyle et al. | |
| 2005/0241639 | A1 * | 11/2005 | Zilberg | A61B 5/4818 128/204.23 |
| 2006/0009704 | A1 | 1/2006 | Okada et al. | |
| 2007/0142741 | A1 | 6/2007 | Berthon-jones et al. | |
| 2007/0293781 | A1 | 12/2007 | Sims et al. | |
| 2008/0015454 | A1 | 1/2008 | Gal | |
| 2008/0255468 | A1 | 10/2008 | Derchak et al. | |
| 2008/0312516 | A1 * | 12/2008 | Ozaki | A61B 5/6887 600/301 |
| 2011/0054341 | A1 | 3/2011 | Jeong et al. | |
| 2012/0246795 | A1 | 10/2012 | Scheffler et al. | |
| 2013/0006075 | A1 * | 1/2013 | Baker, Jr. | A61M 16/026 600/322 |
| 2016/0213287 | A1 | 7/2016 | Kuller | |
| 2018/0256074 | A1 * | 9/2018 | Persidsky | A61B 5/113 |
| 2019/0046087 | A1 * | 2/2019 | Kuller | A61B 5/0826 |

FOREIGN PATENT DOCUMENTS

| | | | |
|---|---|---|---|
| WO | WO-2015187642 | A1 | 12/2015 |
| WO | WO-2022226028 | A1 | 10/2022 |

OTHER PUBLICATIONS

"U.S. Appl. No. 15/091,294, Advisory Action mailed Mar. 2, 2017", 3 pgs.

"U.S. Appl. No. 15/091,294, Examiner Interview Summary mailed Aug. 4, 2017", 2 pgs.

"U.S. Appl. No. 15/091,294, Final Office Action mailed Dec. 11, 2017", 24 pgs.

"U.S. Appl. No. 15/091,294, Final Office Action mailed Dec. 12, 2016", 19 pgs.

"U.S. Appl. No. 15/091,294, Non Final Office Action mailed May 4, 2017", 22 pgs.

"U.S. Appl. No. 15/091,294, Non Final Office Action mailed Aug. 12, 2016", 14 pgs.

"U.S. Appl. No. 15/091,294, Notice of Allowance mailed Jul. 18, 2018", 9 pgs.

"U.S. Appl. No. 15/091,294, Response filed Feb. 9, 2017 to Final Office Action mailed Dec. 12, 2016", 14 pgs.

"U.S. Appl. No. 15/091,294, Response filed Feb. 26, 2018 to Final Office Action mailed Dec. 11, 2017", 15 pgs.

"U.S. Appl. No. 15/091,294, Response filed Mar. 9, 2017 to Advisory Action mailed Mar. 2, 2017", 15 pgs.

"U.S. Appl. No. 15/091,294, Response filed Sep. 5, 2017 to Non Final Office Action mailed May 4, 2017", 14 pgs.

"U.S. Appl. No. 15/091,294, Response filed Oct. 3, 2016 to Non Final Office Action mailed Aug. 12, 2016", 9 pgs.

"U.S. Appl. No. 16/159,980, Non Final Office Action mailed May 25, 2022", 16 pgs.

"U.S. Appl. No. 16/159,980, Preliminary Amendment filed Dec. 12, 2019", 7 pgs.

"European Application Serial No. 15802955.3, Communication Pursuant to Article 94(3) EPC mailed Apr. 15, 2019", 7 pgs.

"European Application Serial No. 15802955.3, Communication Pursuant to Article 94(3) EPC mailed Sep. 21, 2021", 7 pgs.

"European Application Serial No. 15802955.3, Extended European Search Report mailed Dec. 12, 2017", 8 pgs.

"European Application Serial No. 15802955.3, Response filed Jul. 17, 2018 to Extended European Search Report mailed Dec. 12, 2017", 13 pgs.

"European Application Serial No. 15802955.3, Response filed Oct. 17, 2019 to Communication Pursuant to Article 94(3) EPC mailed Apr. 15, 2019", 6 pgs.

"European Application Serial No. 15802955.3, Response filed Oct. 25, 2021 to Communication Pursuant to Article 94(3) EPC mailed Sep. 21, 2021", 10 pgs.

"International Application Serial No. PCT/US2015/033703, International Preliminary Report on Patentability mailed Dec. 15, 2016", 7 pgs.

"International Application Serial No. PCT/US2015/033703, International Search Report mailed Sep. 16, 2015", 2 pgs.

"International Application Serial No. PCT/US2015/033703, Written Opinion mailed Sep. 16, 2015", 5 pgs.

Lukocius, et al., "The Respiration Rate Estimation Method based on the Signal Maximums and Minimums Detection and the Signal Amplitude Evaluation", Elektronika ir Elektrotechnika, vol. 88, No. 8, (2008), 4 pgs.

"International Application Serial No. PCT/US2022/025489, International Search Report mailed Jul. 18, 2022", 4 pgs.

"International Application Serial No. PCT/US2022/025489, Written Opinion mailed Jul. 18, 2022", 8 pgs.

"U.S. Appl. No. 16/159,980, Response filed Aug. 5, 2022 to Non Final Office Action mailed May 25, 2022", 12 pgs.

"U.S. Appl. No. 16/159,980, Final Office Action mailed Nov. 25, 2022", 18 pgs.

* cited by examiner

BREATH VOLUME MONITORING SYSTEMS AND METHODS

CROSS-REFERENCE TO RELATED APPLICATION(S)

The present disclosure claims priority to Provisional Application No. 63/201,275, entitled "Breath Volume Monitoring Systems and Methods," and filed Apr. 21, 2021, the contents of which are hereby incorporated by reference herein in their entirety.

TECHNICAL FIELD

The invention relates to monitoring systems and methods for measuring one or more physiological parameters of an individual. More particularly, the invention relates to systems and methods for monitoring one or more parameters or other data relating to the breath volume of an individual, determining various breath characteristics or indicators based on breath volume data, and providing a meaningful display of the breath characteristics or indicators for easy and quick identification and/or diagnosis of breathing-related or other health conditions.

BACKGROUND

Patients are often treated for diseases and/or conditions associated with a compromised status of the patient, for example, a compromised physiologic status. Such conditions may include sleep apnea, which is implicated in atrial fibrillation, hypertension, and chronic fatigue; sleep hypopnea; heart failure; asthma; chronic obstructive pulmonary disease; and others. In some instances, a patient may report symptoms that require diagnosis to determine the underlying cause. In such cases, long term monitoring of the patient can provide useful information as to the physiologic status of the patient. In some instances, a patient may have been hospitalized and monitoring is necessary in the intensive care unit or post-anesthesia.

There are several types of devices, such as a Holter monitor, or ambulatory electrocardiography device, that may be used for long term monitoring of a patient. However, conventional devices, such as the Holter monitor, may not collect all of the kinds of data that would be desirable or ideal to diagnose, for example, respiration rate or tidal volume of the patient, thus making it generally ineffective for diagnosing and/or treating certain conditions such as apnea and hypopnea. In addition, because many conventional devices, such as a Holter monitor, are uncomfortable and bulky, the result may be a "non-compliant" patient or individual that refuses to properly wear the device, and thus, any data collected may be incomplete, unusable, or less than ideal.

Moreover, the data provided by conventional devices is often generally raw measurement data. Typically, an expert or specialist must tediously review and interpret the raw measurement data. This is often time consuming and is a less than desirable experience.

Thus, a need exists for improved monitoring systems and methods that are capable of providing accurate respiratory volumetric dynamics data and that overcome the shortcomings of conventional methods and devices. There is a further need for improved systems and methods for monitoring one or more parameters or other data relating to the breath volume of an individual, determining various breath characteristics or indicators based on breath volume data, and providing a meaningful display of the breath characteristics or indicators for easy and quick identification of breathing patterns and/or related diagnosis of breathing-related or other health conditions.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

DETAILED DESCRIPTION

The invention relates to improved monitoring systems and methods for measuring one or more physiological parameters of an individual. More particularly, the invention relates to improved systems and methods for monitoring one or more parameters or other data relating to the breath volume of an individual, determining various breath characteristics or indicators based on breath volume data, and providing a meaningful display of the breath characteristics or indicators for easy and quick identification and/or diagnosis of breathing-related or other health conditions.

Figure 1:
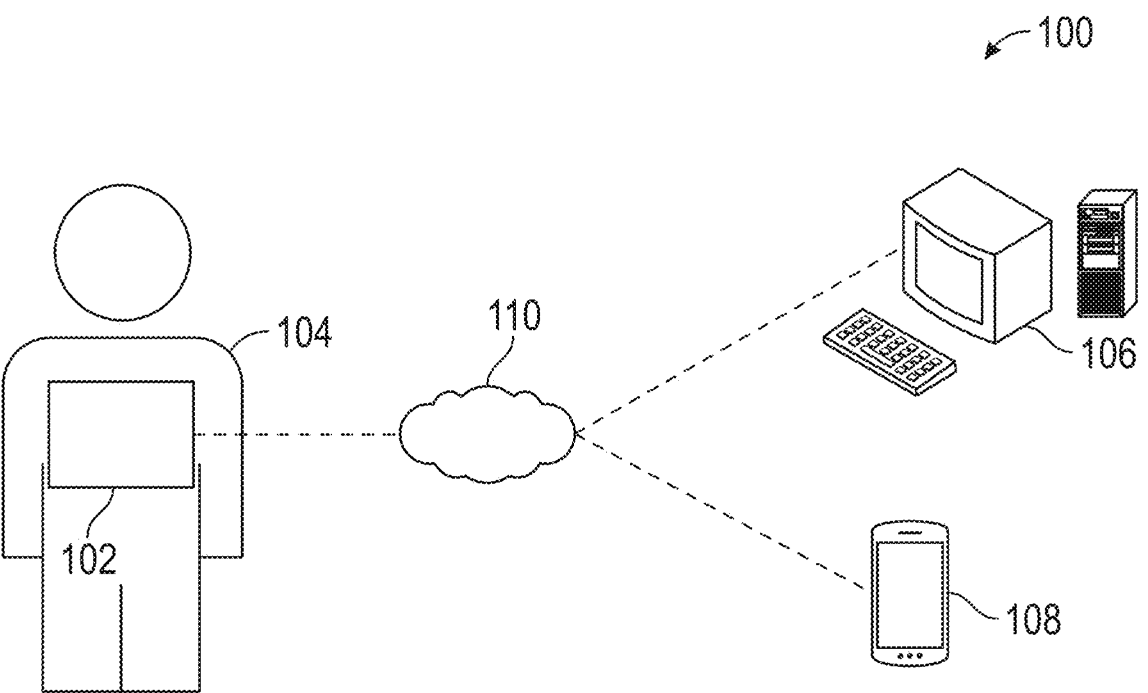
FIG. 1 illustrates an example system in accordance with the present disclosure.

FIG. 1 depicts various components of a system 100 in accordance with the present disclosure. System 100 may include a monitoring device 102, which may be worn by a user or patient 104 for collecting raw breath data and/or other physiological parameters of the user 104. Continuously, periodically, randomly, or at select times, monitoring device 102 may be communicatively connected with computation system 106 or other computational device 108, such as a mobile electronic device (e.g., smartphone, tablet, laptop computer, wearable electronic device, etc.). Monitoring device 102 may be communicatively connected with computation system 106 (e.g., desktop computer, server, etc.) or other computational device 108 via a wired or wireless network 110. Example networks can include a local area network (LAN), a wide area network (WAN), a packet data network (e.g., the Internet), mobile telephone networks (e.g., cellular networks), Plain Old Telephone (POTS) networks, wireless data networks (e.g., networks based on the IEEE 802.11 family of standards known as Wi-Fi or the IEEE 802.16 family of standards known as WiMax), networks based on the IEEE 802.15.4 family of standards, and peer-to-peer (P2P) networks, among others. Monitoring device 102 may additionally or alternatively communicate with computation system 106 or other computational device 108, for example, using radio frequency (RF) or personal area network (PAN) technologies, such as the IEEE 802.15.1, Bluetooth, Bluetooth Low Energy (BLE), near field communications (NFC), ZigBee, GSM, CDMA, ultra-wideband (UWB), etc.

Monitoring device 102 may be any suitable device for monitoring or measuring one or more physiological parameters of the user 104. For instance, Respiratory Inductance Plethysmography (RIP) is a method of evaluating pulmonary ventilation by measuring the movement of the chest and abdominal wall. Accurate measurement of pulmonary ventilation or breathing often requires the use of devices such as masks or mouthpieces coupled to the airway opening. While such devices may be used as monitoring device 102 of the present disclosure, these devices are often both encumbering and invasive, and are not generally well suited for continuous or ambulatory measurements. Other suitable RIP devices sense respiratory excursions at the body surface and can be used to measure pulmonary ventilation. Sensor methodologies based on this theory using, for example, dual elastic bands have been developed. An elastic transducer band of this type may typically include embroidered sinusoid wire coils that are insulated by fabric in a lightweight elastic and adhesive band. The dual transducer bands may be placed on a user with one generally around the rib cage under the armpits and another around the abdomen at the level of the umbilicus (belly button). The bands are connected to an oscillator and subsequent frequency demodulation electronics to obtain digital waveforms. During inspiration, the cross-sectional area of the rib cage and abdomen of the user increases, altering the self-inductance of the coils and the frequency of their oscillation, with the increase in cross-sectional area proportional to lung volume. Electronics convert this change in frequency to a digital respiration waveform where the amplitude of the waveform is proportional to the inspired breath volume.

More recently, similar technology has been incorporated into stretch garments and bands. An example of such a device, which may be used as monitoring device 102 of the present disclosure, is described in U.S. Pat. No. 10,123,724, titled "Breath Volume Monitoring System and Method," which is hereby incorporated herein by reference in its entirety.

Figure 2A:
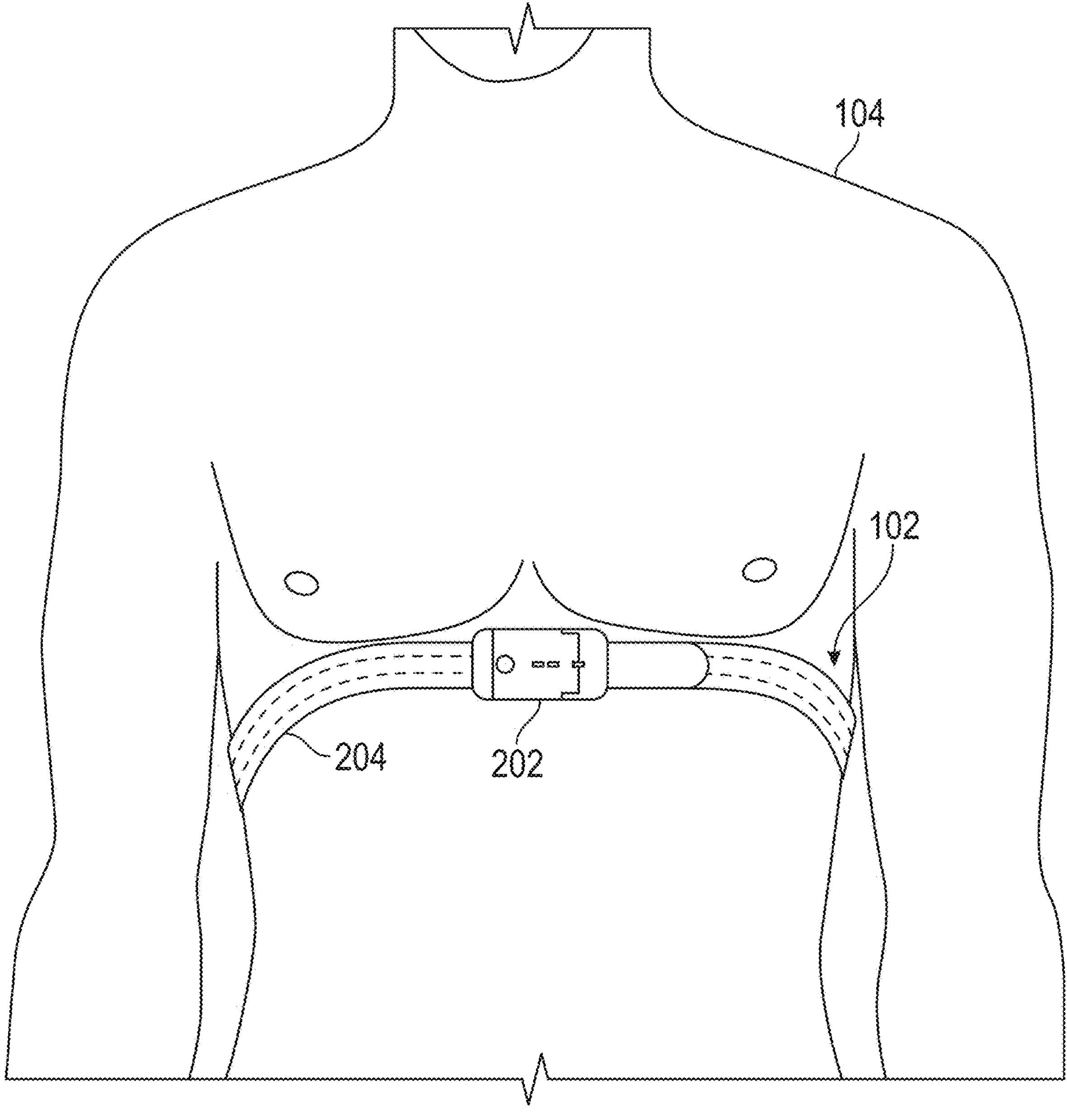
FIGS. 2*a-c* illustrate example monitoring devices in accordance with the present disclosure.
Figure 2B:
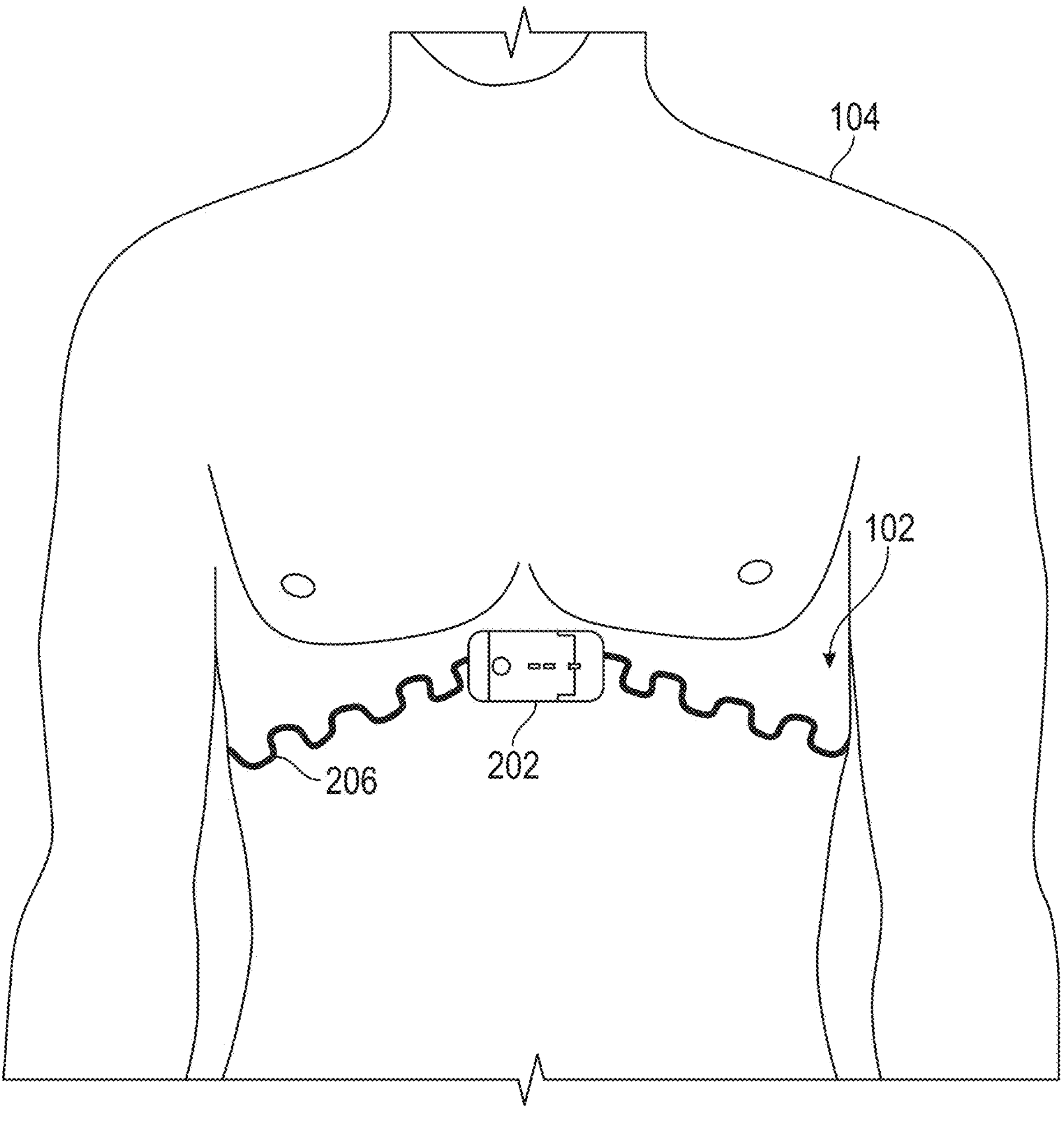
Figure 2C:
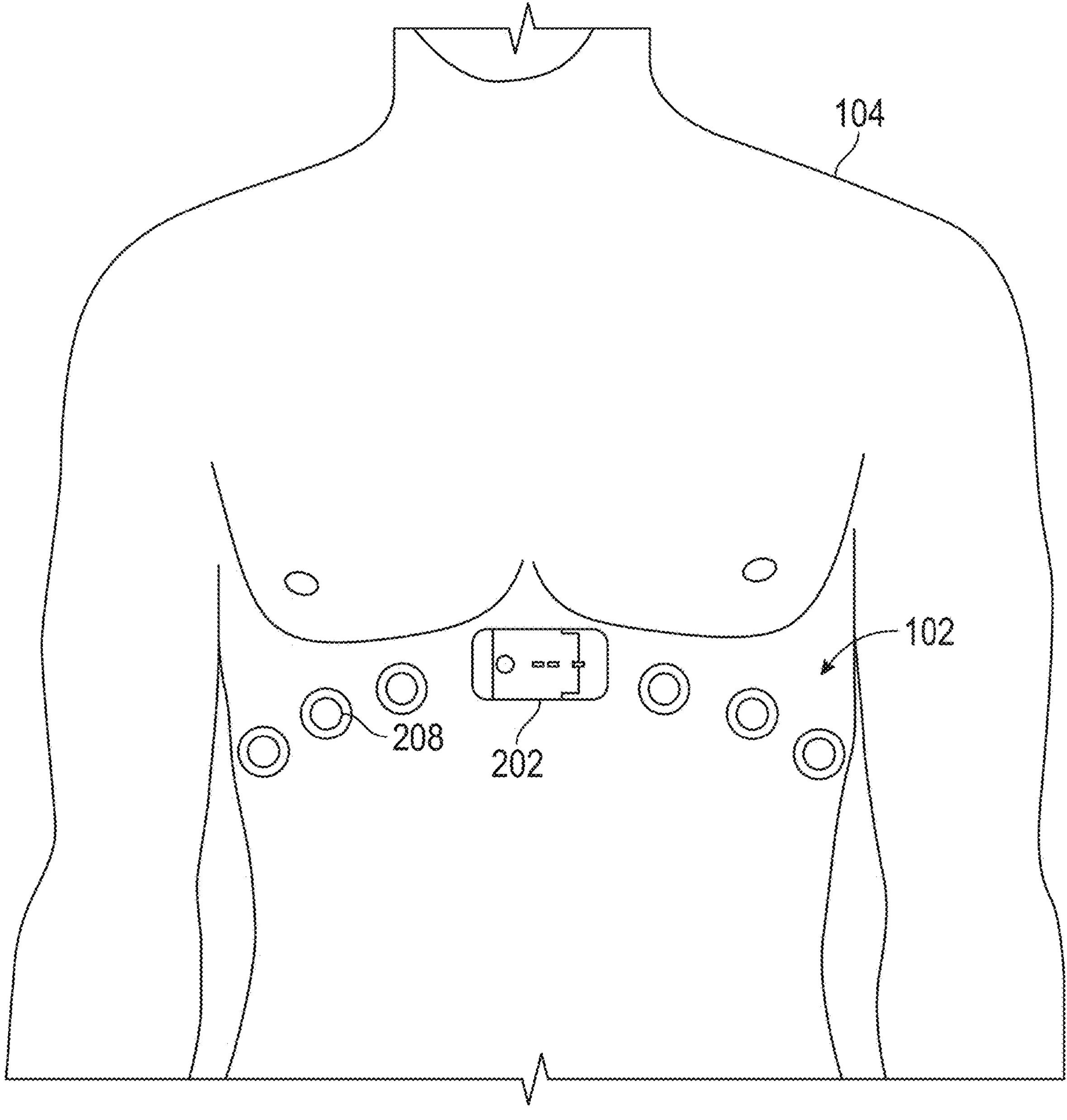

FIG. 2*a* illustrates a non-limiting example of monitoring device 102. Monitoring device 102 may comprise a housing 202 enclosing a microprocessor or other computational means. The housing 202 and microprocessor or other computational means may be operably coupled to a knitted silver, conductive/resistive, elastic, thoracic girth band 204, which has variability in either or both resistance or inductance resulting from changes in stretch/elongation of the band. In general, the microprocessor or other computational means may include an analog to digital converter or other suitable electronic component that converts the spontaneous analog resistance levels of the girth band 204 into numerical representations, thereby generating "raw" sensor data, corresponding to changes in the user's thoracic girth along the meridian of the girth band 204.

Figure 3:
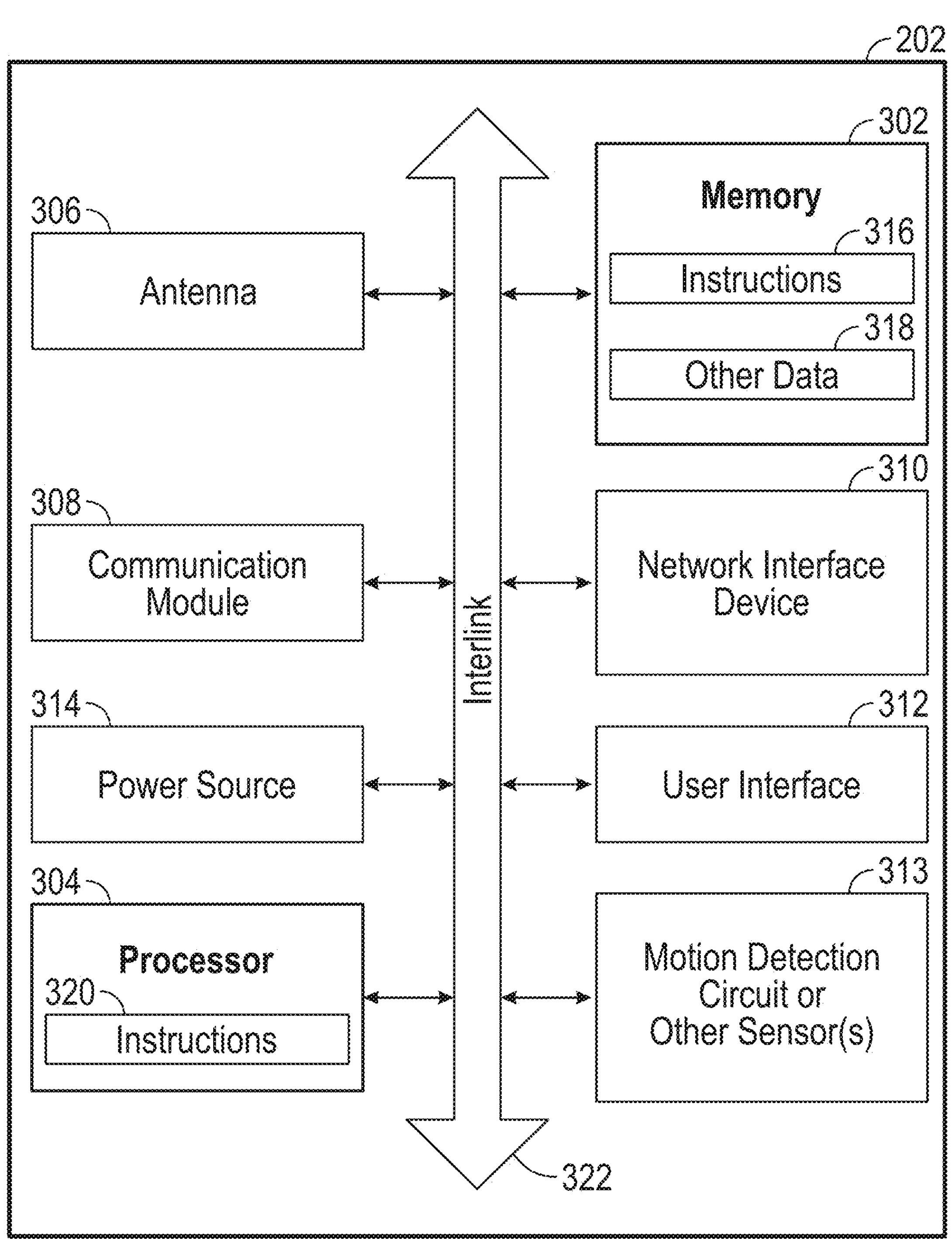
FIG. 3 illustrates a block diagram schematic of various example components housed by an example monitoring device in accordance with the present disclosure.

FIG. 3 is a block diagram schematic that more specifically illustrates various example components that may be housed by housing 202. It is understood that not all the components illustrated in FIG. 3 and described with respect thereto are required and that other components, in addition to those illustrated in FIG. 3, may be included. In general, the various components within housing 202 can include one or more of a memory 302, a processor 304, one or more antennas 306, a communication module 308, a network interface device 310, a user interface 312, a motion detection circuit or other sensor(s) 313, and a power source or supply 314.

Memory 302 can be used in connection with the execution of application programming or instructions by processor 304, and for the temporary or long-term storage of program instructions or instruction sets 316 and/or other data 318, such as "raw" sensor data or data determined using "raw" sensor data, as will be described in further detail below. For example, memory 302 can contain executable instructions 316 that are used by the processor 304 to run other components within housing 202 and/or to determine other such data using "raw" sensor data. Memory 302 can comprise a computer readable medium that can be any medium that can contain, store, communicate, or transport data, program code, or instructions for use by or in connection with processor 304. The computer readable medium can be, for example but is not limited to, an electronic, magnetic, optical, electromagnetic, infrared, or semiconductor system, apparatus, or device. More specific examples of suitable computer readable medium include, but are not limited to, an electrical connection having one or more wires or a tangible storage medium such as a hard disk, a random access memory (RAM), a read-only memory (ROM), an erasable programmable read-only memory (EPROM or EEPROM), Dynamic RAM (DRAM), or any solid-state storage device, in general. Computer readable media includes, but is not to be confused with, computer readable storage medium, which is intended to cover all physical, non-transitory, or similar embodiments of computer readable media.

Processor 304 can correspond to one or more computer processing devices or resources. For instance, processor 304 can be provided as silicon, as a Field Programmable Gate Array (FPGA), an Application-Specific Integrated Circuit (ASIC), any other type of Integrated Circuit (IC) chip, a collection of IC chips, or the like. As a more specific example, processor 304 can be provided as a microprocessor, Central Processing Unit (CPU), or plurality of microprocessors or CPUs that are configured to execute instruction sets stored in an internal memory 320 and/or memory 302.

Antenna 306 can correspond to one or multiple antennas and can be configured to facilitate wireless communication between monitoring device 102 and another device such as computation system 106 or computational device 108. Antenna(s) 306 can be arranged to operate using one or more wireless communication protocols and operating frequencies including, but not limited to, the IEEE 802.15.1, Bluetooth, Bluetooth Low Energy (BLE), near field communications (NFC), ZigBee, GSM, CDMA, Wi-Fi, RF, ultra-wideband (UWB), and the like. By way of example, antenna(s) 306 can include an RF antenna, and as such, may transmit/receive RF signals through free-space to be received/transferred by another device, such as computation system 106 or computational device 108, having an RF transceiver.

Communication module 308 can be configured to communicate according to any suitable communication protocol with one or more different systems or devices either remote or local to monitoring device 102, such as computation system 106 or computational device 108. In an example, communication module 308 or other component within housing 202 may comprise a USB port for direct connection via a USB cable, or other similar physical jack/port and physical transfer cable, to such other system(s), such as computation system 106 or computational device 108.

Network interface device 310 includes hardware to facilitate communications with other devices, such as computation system 106 or computational device 108, over a communication network, such as network 110, utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a personal area network (PAN), such as the IEEE 802.15.1, Bluetooth, Bluetooth Low Energy (BLE), near field communications (NFC), ZigBee, GSM, CDMA, ultra-wideband (UWB), etc., a packet data network (e.g., the Internet), mobile telephone networks (e.g., cellular networks), Plain Old Telephone (POTS) networks, wireless data networks (e.g., networks based on the IEEE 802.11 family of standards known as Wi-Fi or the IEEE 802.16 family of standards known as WiMax), networks based on the IEEE 802.15.4 family of standards, and peer-to-peer (P2P) networks, among others. In some examples, network interface device 310 can include an Ethernet port or other physical jack, a USB port, a Wi-Fi card, a Network Interface Card (NIC), a cellular interface (e.g., antenna, filters, and associated circuitry), or the like. In some examples, network interface device 310 can include one or more antennas to wirelessly communicate using at least one of single-input multiple-output (SIMO), multiple-input multiple-output (MIMO), or multiple-input single-output (MISO) techniques.

User interface 312 can include one or more input devices and/or output devices. Examples of suitable user input devices that can be included in user interface 312 include, without limitation, one or more buttons, a keypad, a touch-sensitive surface, a stylus, a camera, a microphone, touch screen, fingerprint reader, etc. Examples of suitable user output devices that can be included in user interface 312 include, without limitation, one or more LEDs, a LCD panel, a display screen, a touchscreen, one or more lights, a speaker, etc. It should be appreciated that user interface 312 can also include a combined user input and user output device, such as a touch-sensitive display or the like.

Motion detection circuit 313 may include one or more suitable sensors for detecting motion and/or determining position, such as one or more of an accelerometer, gyroscope, rotation sensor, magnetic field sensor, etc. In one example, motion detection circuit 313 may comprise a nine-axis motion detector having a three-axis accelerometer, a three-axis rotation sensor, and a three-axis magnetic field sensor. The motion detection circuit 313 may provide movement and postural orientation data points to augment the breath data in the context of the user's posture and movements. Motion detection circuit 313 may be suitable as, or alternatively or additionally include, an actigraph unit for monitoring actigraphy. In addition to or alternative to motion detection circuit 313, any other suitable sensor(s) may be provided within housing 202. For example, other sensor(s) 313 may include a temperature sensor (such as a skin temperature sensor), heart rate sensor, or blood pressure sensor or monitoring device.

Power source 314 can be any suitable internal power source, such as a battery, capacitive power source or similar type of charge-storage device, etc., and/or can include one or more power conversion circuits suitable to convert external power into suitable power (e.g., conversion of externally-supplied AC power into DC power) for components within the housing 202. Power source 314 can also include some implementation of surge protection circuitry to protect the components within housing 202 from power surges.

One or more interlinks or buses 322 operable to transmit communications between the various hardware components of the monitoring device 102 may also be provided. A system bus 322 can be any of several types of commercially available bus structures or bus architectures.

With reference back to FIG. 2*a*, the monitoring device 102 may be positioned on the user 104 such that the housing 202 is just over the chest plate area of the user 104 just above the bottom of the user's sternum. The girth band 204 may connect to a first side of the housing 202, encircle the user's 104 torso around the user's thorax in such a way that it follows the lowest floating rib, or the groove just above the lowest floating rib, of the lower ribcage, and connect to a second side of the housing. That is, the girth band 204 may encircle the user's 104 torso with the band higher at the front side of the user and sashaying lower at the backside of the user. In an example, the girth band 204 may be positioned such that, for at least a portion of the backside of the user, the girth band sits, or passes, generally at the level where the user's lowest floating ribs join the user's vertebrae. The foregoing described general position of the girth band 204 may be referred to herein as the "desired meridian" of the user 104. The desired meridian is effective for measuring three different types of breaths-intercostal, diaphragmatic, and mixed intercostal/diaphragmatic. All three types of breaths have a significant impact on this meridian unlike any other circumference point (e.g., armpits, across nipples, around abdomen where heart monitor bands are typically placed). This meridian also provides a good balance between comfort, accuracy, and consistency of placement against slippage. This meridian has also proven to work on all sizes and shapes of humans, from newborns to extremely obese adults.

The microprocessor or other computational means of the housing 202 may be operably coupled to the girth band 204, which as stated above, may comprise a knitted silver, conductive/resistive elastic, which has variability in either or both resistance or inductance resulting from changes in stretch/elongation of the band. In some examples, the girth band 204 has two ends, with each end operably coupled with the microprocessor or other computational means of the housing 202 and electronically coupled with the microprocessor or other computational means of the housing sufficiently to measure girth band resistance levels. In some examples, the girth band 204 may be continuous or comprise a closing mechanism, such as a hook/latch, snap, clip, buckle, or other type of closure, allowing the girth band to form a continuous loop around the user's 104 torso, and the housing 202 may attach or clip onto the girth band, operably connecting the microprocessor or other computational means to the girth band. In some examples, the housing 202 may comprise of two or more portions and a closing mechanism, such as a hook/latch, snap, clip, buckle, or other type of closure, may be provided to connect the two or more portions of the housing, thereby securing the girth band around the user's 104 torso. In some examples, the housing 202 need not be positioned on the band 204 at just above the bottom of the user's 104 sternum and instead, the housing 202 may be positioned anywhere along the girth band around the user's torso, for example, anywhere along the desired meridian, described above. For example, if a user regularly sleeps on his or her stomach, the sternum placement of the housing 202 may prove slightly less comfortable than positioning the housing slightly to the left or the right of the sternum. As another example, there may be circumstances where it is more comfortable for the housing 202 to be placed somewhere around the lower back of a user. The monitoring device 102 may be worn by the user 104 directly against the skin, over a layer of clothing, or between layers of clothing. In use, the girth band 204 may be tensioned or pre-tensioned (for example, through a prior fitting procedure), such that the elasticity of the girth band ensures a fit around the user's 104 torso that will not dislocate the girth band 204 during daily activity, such as walking, sleeping, etc. In some examples, a slightly sticky or tacky backing may be provided on at least a portion of a backside or user facing side of the housing 202 and/or any portion or portions of the user facing side of the girth band 204 to help keep the monitoring device 102 in place over time. The slightly sticky or tacky backing may be, for example but not limited to, Gecko® Nanoplast® or Gecko®-Tape by Gottlieb Binder GmbH & Co. KG.

In some example embodiments, as illustrated in FIG. **2*b*, the monitoring device 102 or girth band 204 may comprise a noninvasive, wearable device mounted on the user's 104 skin, such as an electronic "tattoo" or e-tattoo 206, also referred to as epidermal electronics. Such epidermal electronics 206 may generally comprise ultra-thin and ultra-soft, noninvasive, skin-conformable devices that may be temporarily applied, such as with stretchable adhesives, to the user's skin. Such an epidermal electronic device may be positioned around the user's 104 torso, such as along the desired meridian, and may be used to monitor, e.g., periodically or continuously, variability in either or both resistance or inductance proportional to stretch along the user's 104 torso, such as along the desired meridian. The microprocessor or other computational means of the monitoring device 102 may be incorporated into such epidermal electronic device or may be housed in a housing, such as housing 202**, which may be attached to the epidermal electronic device.

In other example embodiments, as illustrated in FIG. **2*c*, the monitoring device 102 or girth band 204 may comprise a plurality of independent adhesive sensors 208 placed at even, uneven, or random intervals around the user's 104 torso, such as along the desired meridian. Each sensor 208 may be able to determine a distance between it and one or more of its neighboring sensors and may communicate this data, e.g., periodically, continuously, dynamically, or randomly, as it changes through, for example, a wireless network to a primary one of the sensors (e.g., 202**) or other device for storing in memory.

While example devices are described above, any device that measures changes in girth of a user due, at least in part, to breathing and can provide corresponding "raw" sensor data (e.g., numerical representations of user girth measurements or changes), or any device that measures any other physiological parameter(s) from which breath data, such as breath volume may be determined, may be used as monitoring device 102 of the present disclosure.

Figure 4:
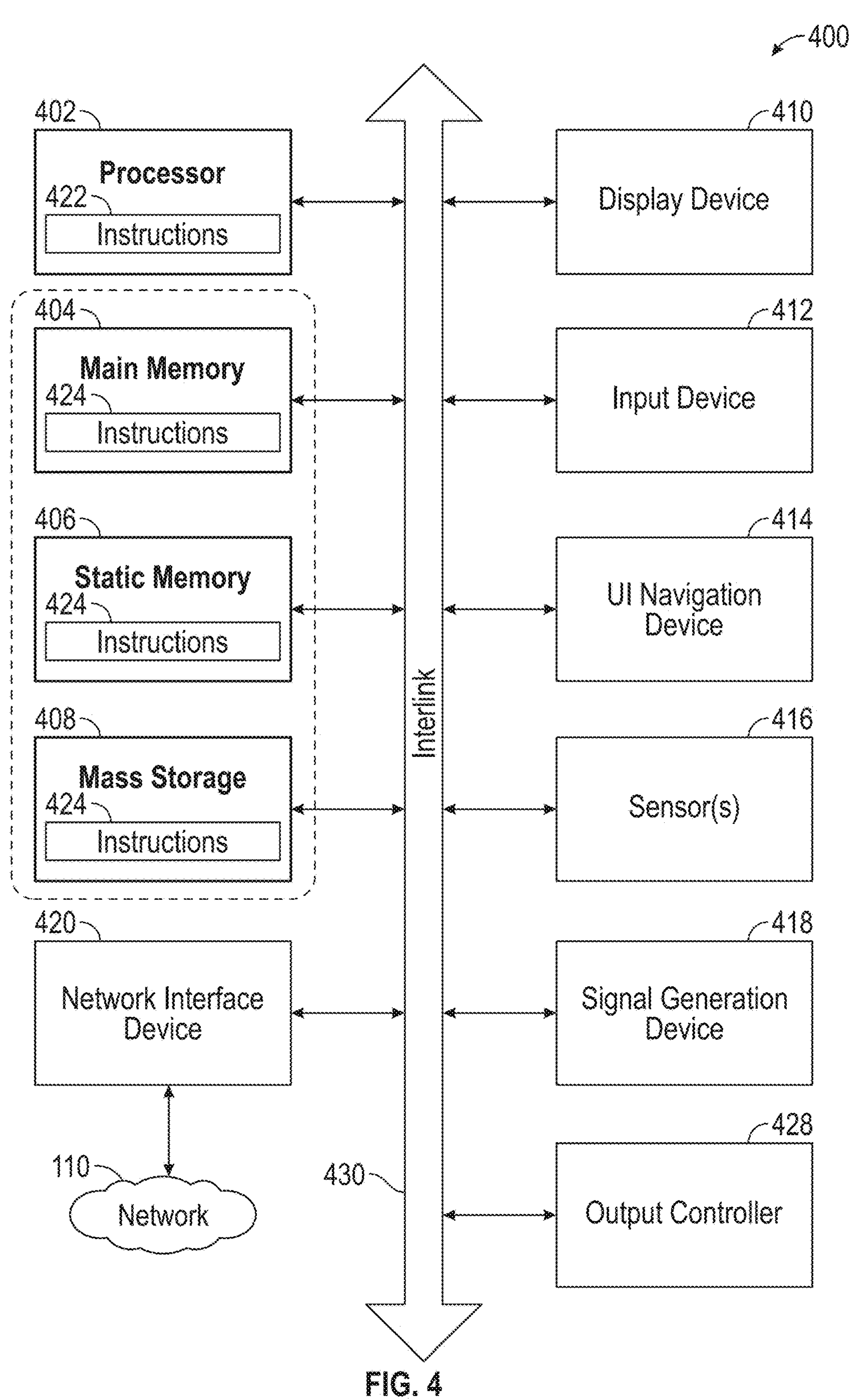
FIG. 4 illustrates a block diagram schematic of various example components of a machine that may be used as, for example, a computation system or other computational device in accordance with the present disclosure.

FIG. 4 illustrates a block diagram schematic of various example components of an example machine 400 that can be used as, for example, computation system 106 or other computational device 108. In some embodiments, machine 400 can operate as a standalone device or can be connected (e.g., networked) to other machines. In a networked deployment, machine 400 can operate in the capacity of a server machine, a client machine, or both in server-client network environments. In some examples, machine 400 can act as a peer machine in a peer-to-peer (P2P) (or other distributed) network environment. Machine 400 can be or include a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 400 can include a hardware processor 402 (e.g., a central processing unit (CPU), a graphics processing unit (GPU), a hardware processor core, or any combination thereof) and a main memory 404, a static memory (e.g., memory or storage for firmware, microcode, a basic-input-output (BIOS), unified extensible firmware interface (UEFI), etc.) 406, and/or mass storage 408 (e.g., hard drives, tape drives, flash storage, or other block devices) some or all of which can communicate with each other via an interlink (e.g., bus) 430. Machine 400 can further include a display device 410 and an input device 412 and/or a user interface (UI) navigation device 414. Example input devices and UI navigation devices include, without limitation, one or more buttons, a keyboard, a touch-sensitive surface, a stylus, a camera, a microphone, etc.). In some examples, one or more of the display device 410, input device 412, and UI navigation device 414 can be a combined unit, such as a touch screen display. Machine 400 can additionally include a signal generation device 418 (e.g., a speaker), a network interface device 420, and one or more sensors 416, such as a global positioning system (GPS) sensor, compass, accelerometer, or other sensor. Machine 400 can include an output controller 428, such as a serial (e.g., universal serial bus (USB), parallel, or other wired or wireless (e.g., infrared (IR), NFC, etc.) connection to communicate or control one or more peripheral devices (e.g., a printer, card reader, etc.).

Processor 402 can correspond to one or more computer processing devices or resources. For instance, processor 402 can be provided as silicon, as a Field Programmable Gate Array (FPGA), an Application-Specific Integrated Circuit (ASIC), any other type of Integrated Circuit (IC) chip, a collection of IC chips, or the like. As a more specific example, processor 402 can be provided as a microprocessor, Central Processing Unit (CPU), or plurality of microprocessors or CPUs that are configured to execute instructions sets stored in an internal memory 422 and/or memory 404, 406, 408.

Any of memory 404, 406, and 408 can be used in connection with the execution of application programming or instructions by processor 402 for performing any of the functionality or methods described herein, and for the temporary or long-term storage of program instructions or instruction sets 424 and/or other data for performing any of the functionality or methods described herein. Any of memory 404, 406, 408 can comprise a computer readable medium that can be any medium that can contain, store, communicate, or transport data, program code, or instructions 424 for use by or in connection with machine 400. The computer readable medium can be, for example but is not limited to, an electronic, magnetic, optical, electromagnetic, infrared, or semiconductor system, apparatus, or device. More specific examples of suitable computer readable medium include, but are not limited to, an electrical connection having one or more wires or a tangible storage medium such as a portable computer diskette, a hard disk, a random access memory (RAM), a read-only memory (ROM), an erasable programmable read-only memory (EPROM or EEPROM), Dynamic RAM (DRAM), a solid-state storage device, in general, a compact disc read-only memory (CD-ROM), or other optical or magnetic storage device. As noted above, computer-readable media includes, but is not to be confused with, computer-readable storage medium, which is intended to cover all physical, non-transitory, or similar embodiments of computer-readable media.

Network interface device 420 includes hardware to facilitate communications with other devices over a communication network, such as network 110, utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, wireless data networks (e.g., networks based on the IEEE 802.11 family of standards known as Wi-Fi or the IEEE 802.16 family of standards known as WiMax), networks based on the IEEE 802.15.4 family of standards, and peer-to-peer (P2P) networks, among others. In some examples, network interface device 420 can include an Ethernet port or other physical jack, a Wi-Fi card, a Network Interface Card (NIC), a cellular interface (e.g., antenna, filters, and associated circuitry), or the like. In some examples, network interface device 420 can include one or more antennas to wirelessly communicate using at least one of single-input multiple-output (SIMO), multiple-input multiple-output (MIMO), or multiple-input single-output (MISO) techniques.

As indicated above, machine 400 can include one or more interlinks or buses 430 operable to transmit communications between the various hardware components of the machine. A system bus 322 can be any of several types of commercially available bus structures or bus architectures.

Figure 5:
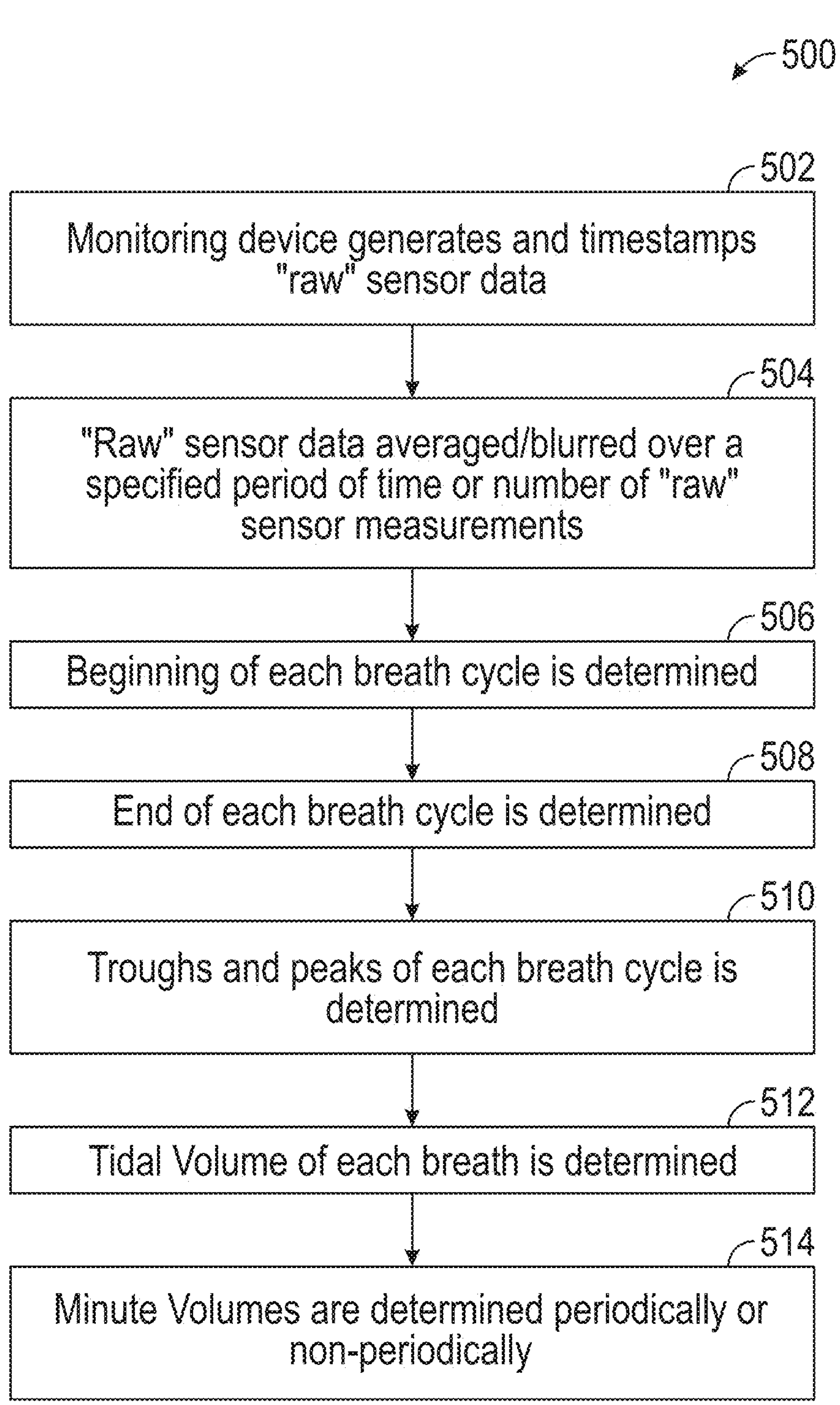
FIG. 5 is a flowchart for determining Tidal Volumes and Minute Ventilation in accordance with an example of the present disclosure.

Turning to FIG. 5, a method 500 of operation of the system 100 is described. For purposes of discussion herein, Tidal Volume (Vte or Vt) may refer to the volume inhaled with each breath. Also for purposes of discussion herein, Minute Ventilation or Minute Volume (referred to herein simply as Minute Ventilation) may be broadly or substantially equivalent to Tidal Volume multiplied by respiratory rate. However, Tidal Volume multiplied by respiratory rate is often an inaccurate approximation in the presence of irregular breathing. Accordingly, according to the present disclosure, Minute Ventilation may be calculated by adding together a sequence of Tidal Volumes over a one minute period of time or any other period of time normalized to one minute.

At step 502, monitoring device 102 may generate "raw" sensor data corresponding to changes in the user's 104 thoracic girth along the meridian of the band 204 (e.g., the desired meridian). For example, as described above, the housing 202 and microprocessor or other computational means of the monitoring device 102 may be operably coupled to a knitted silver, conductive/resistive, elastic thoracic girth band 204, which has variability in either or both resistance or inductance resulting from changes in stretch/elongation of the band. The microprocessor or other computational means of the monitoring device 102 may include an analog to digital converter or other electronic component that converts the spontaneous analog resistance levels of the girth band 204 into numerical representations, thereby generating the "raw" sensor data. In other example embodiments, spontaneous analog resistance levels of the girth band 204 may additionally or alternatively be transmitted to computation system 106 or other computational device 108 for generating the "raw" sensor data. "Raw" sensor data may be collected at any suitable rate or frequency. In some example embodiments, "raw" sensor data may be collected or generated from about 10 times per second to about 1000 times per second or at a frequency of from about 10 Hz to 1 kHz, depending for example, on the intended application. For example, higher frequency sample rates may be useful for "phonocardiogram" analysis of the heart, while lower frequency sample rates may be useful in analyzing breathing disorders. Lower frequency sample rates may also permit longer battery life. The "raw" sensor data may be time-stamped.

The microprocessor or other computational means of the monitoring device 102 may then determine Tidal Volumes based on the "raw" sensor data. Additionally or alternatively, the "raw" sensor data may be generated by, or transmitted to, computation system 106 or other computational device 108, which may then determine Tidal Volumes based on the "raw" sensor data. Steps 504-512 describe an example method for determining Tidal Volumes based on the "raw" sensor data. However, other methods or algorithms for determining Tidal Volumes or Tidal Volume equivalents may be used.

In general, physical girth measurements are, in part, tied to heartbeat and other body articulations or motions, not just the user's breathing cycle. That is, it may not be as simple as looking at the "raw" sensor data both because of potential non-linear behavior of knitted sensors and because of the plethora of other body articulations unrelated to breathing that nonetheless affect girth size measurements. For example, the girth band 204 in accordance with the present disclosure may be sensitive enough to capture the changes in chest size related to the simple beating of the heart. Likewise, many movements involving posture or the use of arms and legs can significantly change the shape of a user's chest and related girth size.

Accordingly, detection of inhale/exhale moments in the "raw" sensor data may not simply be a matter of detecting when the values go up and down. Factors not related to the breath cycle, such as those identified above, may influence the elongation of the girth band 204, causing girth measurement inflections at a much higher frequency than that of the user's breath. As such, averaging or blurring the "raw" sensor data may be used to generally "smooth" out heartbeat and/or other body articulations or factors not related to breath. The resulting smoothed data provides a very good approximation of the breath dynamics.

More particularly, at step 504, the "raw" sensor data may be averaged or blurred over a specified or predetermined period of time or a specified or predetermined number of "raw" sensor measurements. In some example embodiments, "raw" sensor data may be averaged over a period of time of from about the most recent 0.3 seconds to about the most recent 1 or 2 seconds. In some example embodiments, "raw" sensor data may be averaged over about the 3 most recent data readings to about the 10 most recent data readings or even up to about 20-30 or more of the most recent data readings. A sample of averaged "raw" sensor data over a sample period t may be referred to herein as Pt. Each sample, Pt, of averaged "raw" sensor data may be timestamped. Additional discussion of smoothing out the heartbeat and/or other body articulations, and some reasons for doing so, is provided in U.S. Pat. No. 10,123,724, which was previously incorporated herein.

At step 506, the beginning of each breath cycle may be determined. In an example embodiment, for a given breath cycle, the beginning of the breath cycle may be determined based on when an averaged "raw" sensor data sample, Pt, increases from a recent detected trough in the averaged "raw" sensor data by at least a specified or predetermined value, Pi, which in some examples may be 0.1%. The beginning of each breath cycle may be timestamped.

At step 508, the end of each breath cycle may be determined. In an example embodiment, for a given breath cycle, the end of the breath cycle may be determined based on when an averaged "raw" sensor data sample, Pt, is either less than the averaged "raw" sensor data at the beginning of the breath cycle or less than the maximum averaged "raw" sensor data in that breath cycle by at least a specified or predetermined value, Pe, which in some examples may be 0.05%. The end of each breath cycle may be timestamped.

If the end of a breath cycle is determined as occurring before a minimum breath length of a specified or predetermined value, Ps, which in some examples may be about 0.1 second, from the time (e.g., timestamp) of the beginning of that breath cycle, such determined "end" may be discarded, and a new or subsequent end of that breath cycle may be determined, for example, according to the example method described above.

At step 510, the trough and peak of each breath cycle are determined. In an example embodiment, for a given breath cycle, the trough may be determined as the lowest "raw" sensor data within the beginning and end of that breath cycle. The time of occurrence of the trough may be the same as the timestamp of the corresponding lowest "raw" sensor data. In an example embodiment, for a given breath cycle, the peak may be determined as the highest "raw" sensor data within the beginning and end of that breath cycle. The time of occurrence of the peak may be the same as the timestamp of the corresponding highest "raw" sensor data.

At step 512, the Tidal Volume, Vte, of each breath cycle, and thus each breath of the user, may be determined. In an example embodiment, for a given breath cycle or breath of the user, the Tidal Volume for that breath cycle may be determined as the difference between the peak and trough determined for that breath cycle at step 510. In general, in an example embodiment, the averaged/blurred data may be used to determine the beginning and end of a breath cycle while the "raw" sensor data may be used to determine the peak, trough, and Tidal Volume of the breath cycle.

The values for t (for Pt), Pi, Pe, and Ps may each be adjusted or modified for different circumstances or applications to measure different kinds of breathing. For example, these parameters may be tuned or fine-tuned for a particular user to ensure that the girth band 204 is comfortable throughout the fit range and is able to accurately measure from the smallest breaths in reclined deep sleep to the largest breaths in upright activity. As another example, infants and younger people generally breath faster than adults, so these parameters can be tuned to measure faster breathing, which might otherwise be smoothed out for an adult out as heartbeat or motion artefacts. As yet another example, athletic breathing is generally much faster and with more amplitude. Adjusting these parameters enables capturing these breaths without treating them, for example, as heartbeats (which would be faster but with less amplitude). In some embodiments, these parameters can be modified dynamically while monitoring a user, for example, based on information from an accelerometer or other sensor detecting when the user is physically active, and thus, when more dynamic breathing is expected. For example, because some motion artifacts are contemporaneous with peak accelerometer values, such artifacts may, in some cases, be discarded as noise instead of relating to the user's actual breathing pattern.

At step 514, Minute Ventilation may be determined for periodic or non-periodic (e.g., various or prespecified) intervals of the user's monitoring session. In an example embodiment, Minute Ventilation may be determined by aggregating or summing the Tidal Volumes for a series of breath cycles completed within a specified time range, r, and then normalizing to 1 minute based on the time range, r. Any suitable time range, r, may be used, such as but not limited to, 6 seconds, 10 seconds, 15 seconds, 30 seconds, or 60 seconds. In yet another example embodiment, Minute Ventilation may be determined by aggregating or summing the Tidal Volumes for a series of breath cycles completed within a specified time range, r, such as but not limited to, 6 seconds, 10 seconds, 15 seconds, 30 seconds, or 60 seconds. Then, determining the actual amount of time, Tactual, those completed breath cycles took to complete and normalizing to 1 minute based on the actual amount of time, Tactual. Consider an example in which the completed breath cycles occurring within a specified 10 second period actually took only 6 seconds (e.g., Tactual) to complete (e.g., a final breath cycle was greater than 4 seconds, and so didn't complete within the 10 second period). The Tidal Volumes of the completed breath cycles are summed, and the aggregated Tidal Volumes are normalized to 1 minute based on the actual period of time, Tactual, the breath cycles took to complete (i.e., 6 seconds). Therefore, the Minute Ventilation for the specified 10 second period would be the aggregated Tidal Volumes multiplied by 10. Such Minute Ventilation calculation and normalization can be applied to any cluster of breaths. That is, in general, for any cluster of breath cycles, the Tidal Volumes of those breath cycles may be aggregated or summed and then normalized to 1 minute based on the actual amount of time it took for those breath cycles to complete, Tactual.

In addition to Tidal Volume and Minute Ventilation, other metrics may also be determined or estimated. For example, forced expiratory volume (FEV) may be determined or estimated over any suitable time period x, such as over 0.5, 1, 2, or 3 seconds. In an example, FEVx may be determined or estimated by determining the "raw" sensor data for a point in time that is x amount of time after the peak, or highest "raw" sensor data, of the previous breath cycle and then subtracting the determined "raw" sensor data from the peak sensor data of the previous breath cycle. FEVx values may also be timestamped.

While example methods for determining or estimating Tidal Volumes and Minute Ventilation are described herein, any suitable method for determining or estimating Tidal Volumes and Minute Ventilation at periodic, non-periodic, or even random times during a monitoring session of a user may be used.

Figure 6:
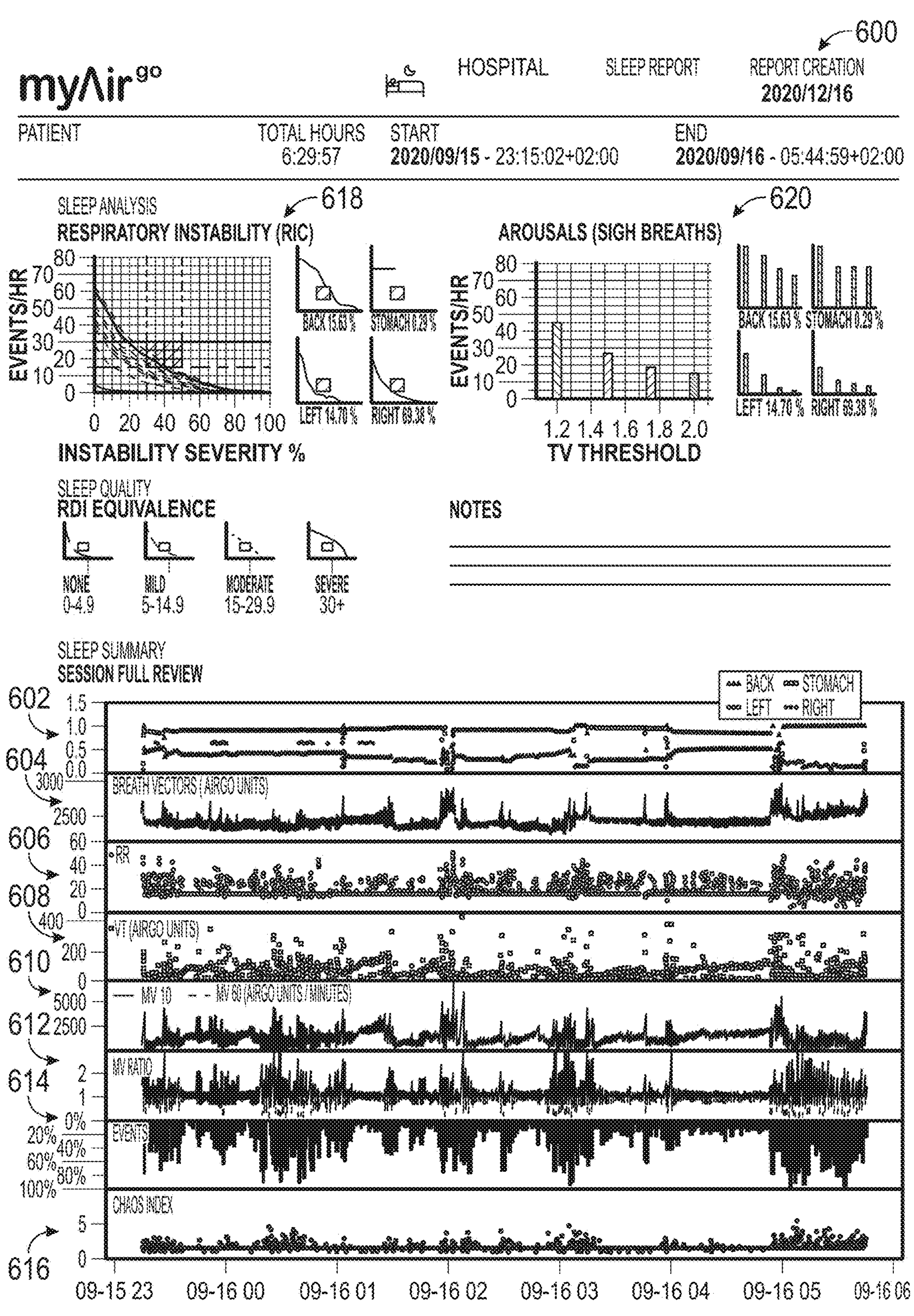
FIG. 6 illustrates various example metrics and visual output that may be determined and displayed based on "raw" sensor data, Tidal Volumes, Minute Ventilation, and/or other data from a monitoring device in accordance with the present disclosure.
Figure 7:
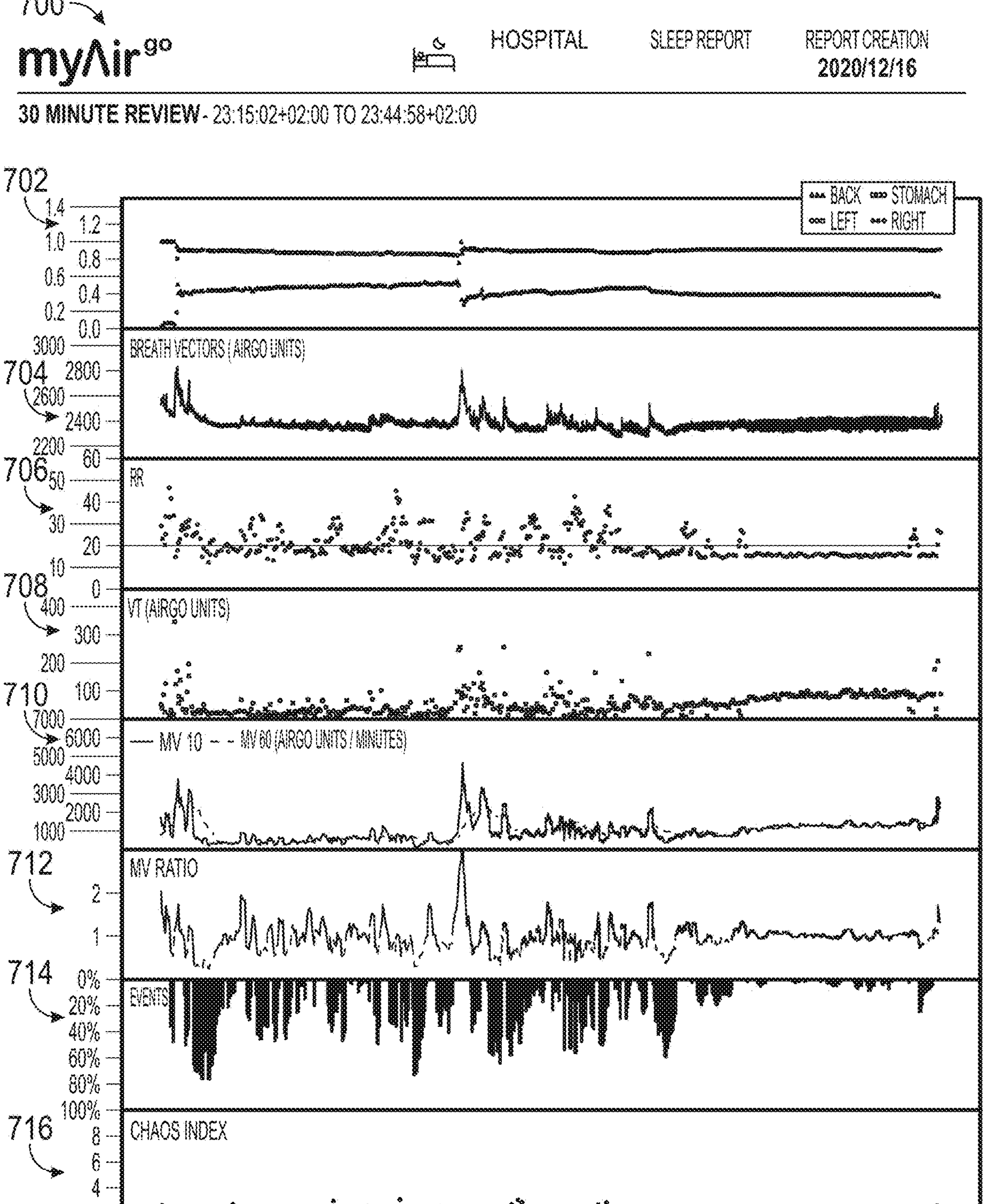
FIG. 7 illustrates an additional example of metrics and visual output that may be determined and displayed based on "raw" sensor data, Tidal Volumes, Minute Ventilation, and/or other data from a monitoring device in accordance with the present disclosure.

FIG. 6 illustrates various example metrics and visual output 600 that may be determined, for example, by the one or more of the systems or devices described herein, and displayed dynamically or statically on, for example, a computer display or other electronic display, or printed out for physical display, based on the "raw" sensor data, Tidal Volumes, Minute Ventilation, and/or other data from the monitoring device, for example, as described above. The metrics/output 600 may include one or more of a position indicator 602, a breath vector display 604, a respiratory rate (RR) display 606, a Tidal Volumes display 608, a Minute Ventilation display 610, a Minute Ventilation Ratio (Mv Ratio) display 612, an events display 614, a Chaos Index display 616, a Respiratory Instability Curve (RIC) display 618, and an arousals display 620, each of which are described in further detail below. As are also described in further detail below, the metrics/output 600 may also include a Rapid Shallow Breathing Index (RSBI) display 1800, a vector slope display 1900, an event duration display 2000, and a Period of time between Instability Events (P-IE) display 2100. In some examples, metrics/output 600 may also include an actigraphy graph showing the user's actigraphy during the monitoring session based on accelerometer measurements obtained from monitoring device 102. An actigraphy graph may be helpful, for example, to distinguish agitated movement during sleep often indicative of arousals or nightmares. Which metrics/output are included in the metrics/output 600 may vary, depending on for example, the purpose of the monitoring session (e.g., a sleep monitoring session to monitor apnea, hypopnea, or other sleep condition, a monitoring session to monitor for Cheyne-Stokes respiration, a monitoring session to monitor a COVID-19 patient, etc.). In an example embodiment, such as illustrated in FIG. 6, the various metrics/output 600 for an entire monitoring session—almost 6.5 hours in the example illustrated—may be shown on a single display or page for quick and easy reference of the entire monitoring session. In some example embodiments, the various metrics/output 6000 may be broken down into smaller portions or chunks of time of the monitoring session, such as 30-minute chunks or any other suitably sized chunks, such as 5-minute, 6-minute, 10-minute, 15-minute, 20-minute chunks, or the like. FIG. 7 is an example metrics and visual output 700 illustrating 30-minute chunks of the position indicator 702, breath vector display 704, RR display 706, Tidal Volumes display 708, Minute Ventilation display 710, My Ratio display 712, Events display 714, and Chaos Index display 716. Of course, the RSBI display 1800, vector slope display 1900, event duration display 2000, P-IE display 2100, and actigraphy may also be broken down into smaller portions or chunks of time and displayed accordingly. The RIC and Arousals displays may also be determined and displayed for smaller portions of time, such as but not limited to 30-minute chunks.

Figures 8A, 8B:
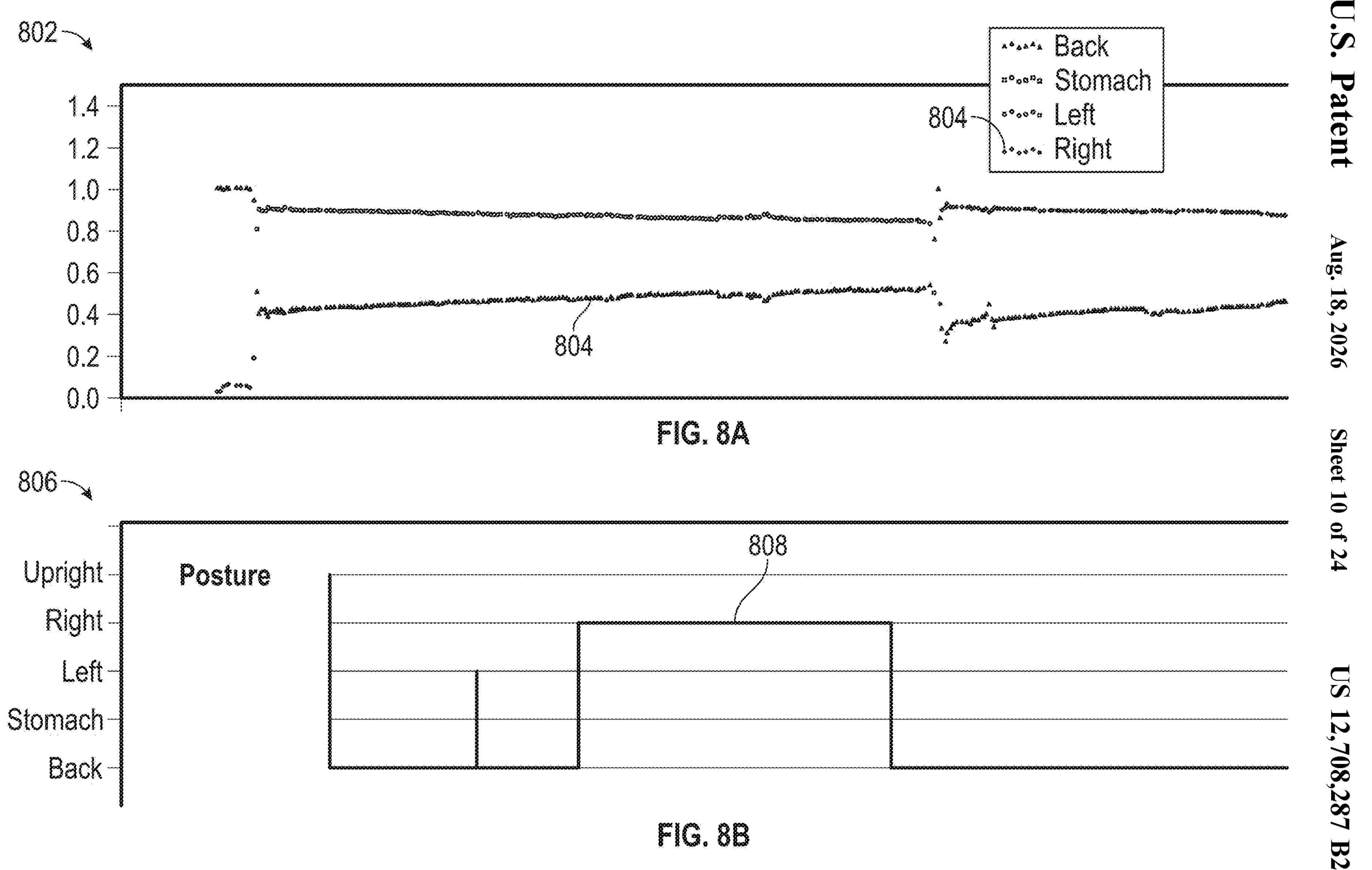
FIG. 8*a* is a magnified view of a portion of an example position indicator in accordance with the present disclosure.
FIG. 8*b* is a magnified view of a portion of another example position indicator in accordance with the present disclosure.

FIG. 8*a* is a magnified view 802 of a portion of a position indicator 602 for purposes of explanation. The position indicator 602/802 illustrates the predominant sleep position (or generally the predominant postural position) of the user at various times during the monitoring session. In FIG. 8*a*, the x-axis corresponds to the time during the monitoring session of the user and the y-axis corresponds to the degree in which the user is in a given sleep position, in this case on a scale of 0.0 to 1.0. However, other scales for the y-axis may be used to represent the degree in which the user is in a given sleep position, such as from 0% to 100%. The position of the user may be determined from, for example, motion detection circuit 313 of monitoring device 102. In an example, the positions of the user may be broken down into 4 general positions-on the back, on the stomach, on the left side, and on the right side. However, in other examples, less, more, or other positions may be included. In an example, the 4 general positions may be grouped into 2 separate datasets, one for determining the degree in which the user is on the back or stomach and one for determining the degree in which the user is on the left or right side. Each position may be associated with a different color, shape, and or size marker 804, and a legend may be provided identifying the markers for each position. As illustrated in FIG. 8*a*, the user's position may be determined at periodic or non-periodic times during the monitoring session and markers 804 may be plotted accordingly with respect to the x- and y-axes. As indicated above, the color, shape, and or size of the marker 804 indicates which position to which the marker corresponds, and the height of the marker corresponds to the degree in which the user is in the given position. In an example, at each time along the x-axis for which the user's position is plotted, both a marker 804 indicating the degree in which the user is on the back or stomach and a marker indicating the degree in which the user is on the left or right side are plotted.

FIG. 8*b* illustrates an alternative example of a position indicator 806. In FIG. 8*b*, the x-axis corresponds to the time during the monitoring session of the user and the y-axis corresponds to the predominant postural position of the user. The postural position of the user may be determined from, for example, motion detection circuit 313 of monitoring device 102. In an example, the postural positions of the user may be broken down into 5 general positions-on the back, on the stomach, on the left side, on the right side, and upright. However, in other examples, less, more, or other postural positions may be included. The user's predominant postural position may be determined at periodic or non-periodic times during the monitoring session. A histogram 808 or similar graph may then be plotted to show the changes in the user's predominant postural position through the monitoring session or portion(s) thereof.

Figure 9:
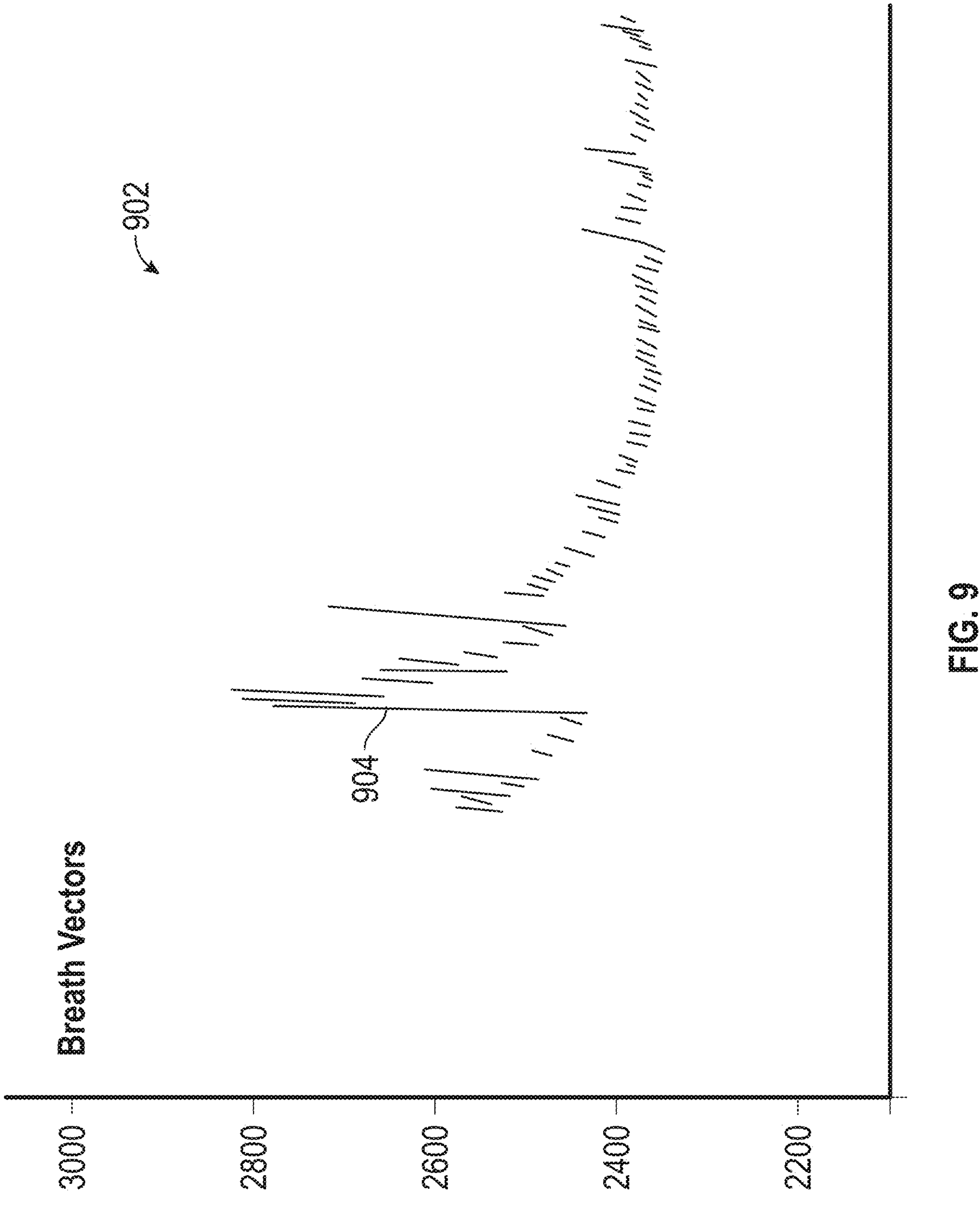
FIG. 9 is a magnified view of a portion of an example breath vectors display in accordance with the present disclosure.

FIG. 9 is a magnified view 902 of a portion of a breath vectors display 604 for purposes of explanation. The breath vectors display 604/902 illustrates each breath cycle as a breath vector 904. In FIG. 9, the x-axis corresponds to the time during the monitoring session of the user and the y-axis corresponds to volume. For each breath cycle, the initial or starting point of the breath vector is the trough of that breath cycle determined at, for example, step 510 and is plotted at the time corresponding to the timestamp of the trough. For each breath cycle, the end point of the breath vector is the peak of that breath cycle determined at, for example, step 510 and is plotted at the time corresponding to the timestamp of the peak. The height of a breath vector 904 (e.g., the value at the peak less the value at the trough) corresponds to the Tidal Volume for the corresponding breath cycle, and the width of the breath vector (e.g., the timestamp at the peak less the timestamp at the trough) corresponds to inhalation time (Tinh) for the breath cycle. Tinh can be an important metric for understanding how panicked a user is in their breathing. The slope of a breath vector 904 corresponds to inhalation flow rate. The relative vertical position of a breath vector 904 corresponds to hyper/hypo inflation. The space between the starting point of a given breath vector 904 and the next breath vector corresponds to the breath cycle time for the breath cycle corresponding to the given breath vector. The space or gap between the end point of a given breath vector 904 and the starting point of the next breath vector corresponds to the exhalation time for the breath cycle corresponding to the given breath vector. The relative position (e.g., lower to higher and vice versa) is indicative of changes in the Functional Residual Capacity (FRC) of the user. The breath vectors display 604/902 provides an easy to analyze multidimensional, vectorial representation for understanding and visualizing a user's breathing patterns and their related physiological function, providing better diagnostic insight than single dimension "indexes," thereby assisting the learning and documentation process for a doctor to diagnose patients.

Figure 10:
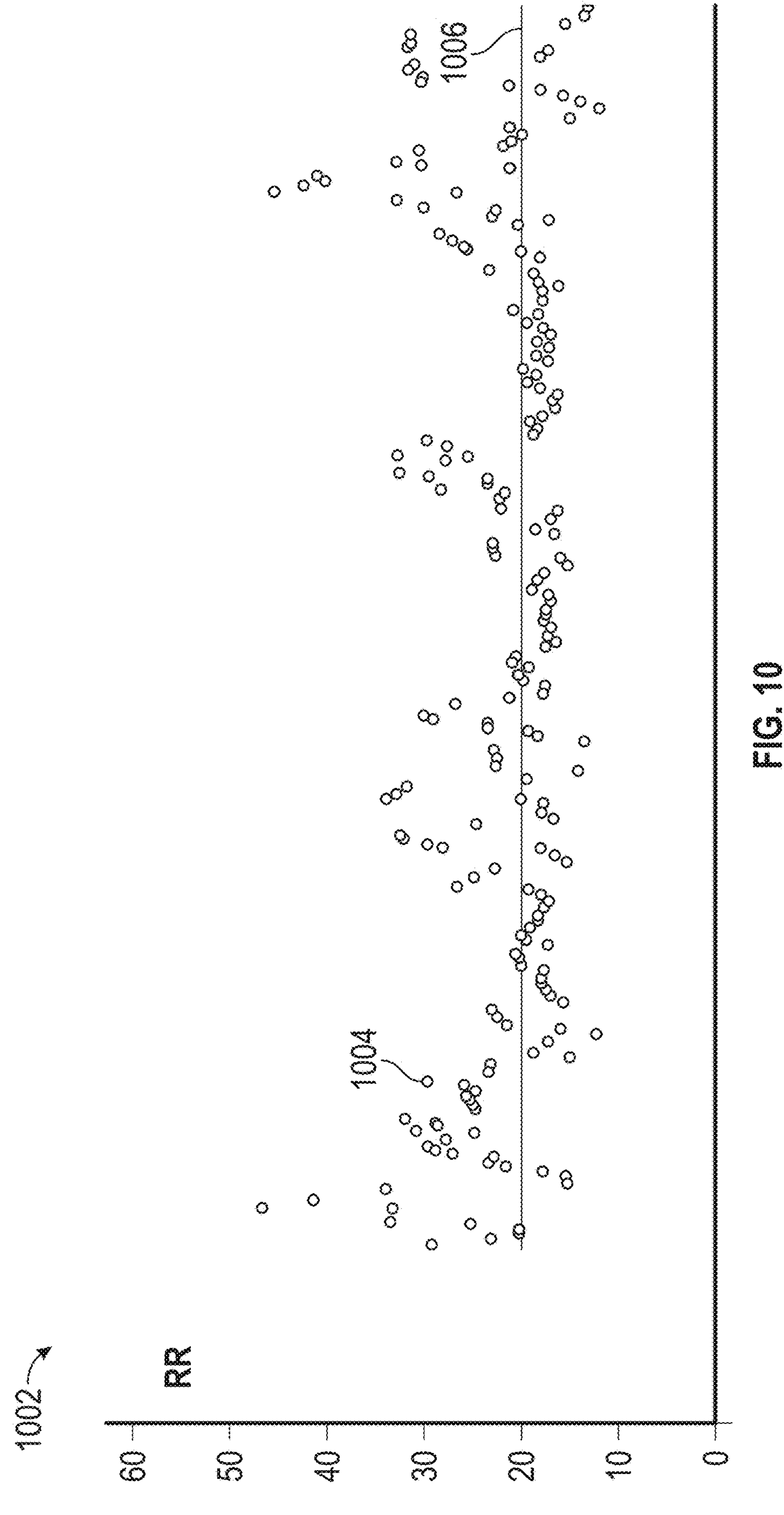
FIG. 10 is a magnified view of a portion of an example respiratory rate display in accordance with the present disclosure.

FIG. 10 is a magnified view 1002 of a portion of an RR display 606 for purposes of explanation. The RR display 606/1002 illustrates the RR for the user calculated or estimated at various periodic or non-periodic times during the monitoring session of the user. Respiratory rate is the number of breaths per minute. The RR may be calculated or estimated by counting the number of breath cycles in the immediately preceding minute or may be calculated or estimated over another longer or shorter immediately preceding period of time, such as 2 minutes, 30 seconds, 10 seconds, etc., and normalized to one minute. In an example, RR may be calculated for each breath. In FIG. 10, the x-axis corresponds to the time during the monitoring session of the user and the y-axis corresponds to the number of breaths per minute. Each RR calculation may be plotted with a marker 1004 on the RR display 606/1002 at the corresponding time along the x-axis. However, other graphical representations, such as a line graph or bar graph, may be used. RR typically drops and stabilizes during deep sleep, becomes fairly random but higher during wakefulness, and random but lower during REM sleep. RR is a fundamental biomarker that can be really important in, for example, determining deep sleep versus REM sleep and analyzing COVID-19 patients. In FIG. 10, a reference line 1006 at around an RR of about 20 may be included. In general, if the RR of the user is above the reference line 1006, the user may generally be considered awake, snoring, or in REM sleep, and if the RR of the user falls below the reference line, the user may generally be considered to be in deep sleep. The reference line 1006 may be located at a different RR or another reference line may be added at a different RR for analyzing other conditions.

Figure 11:
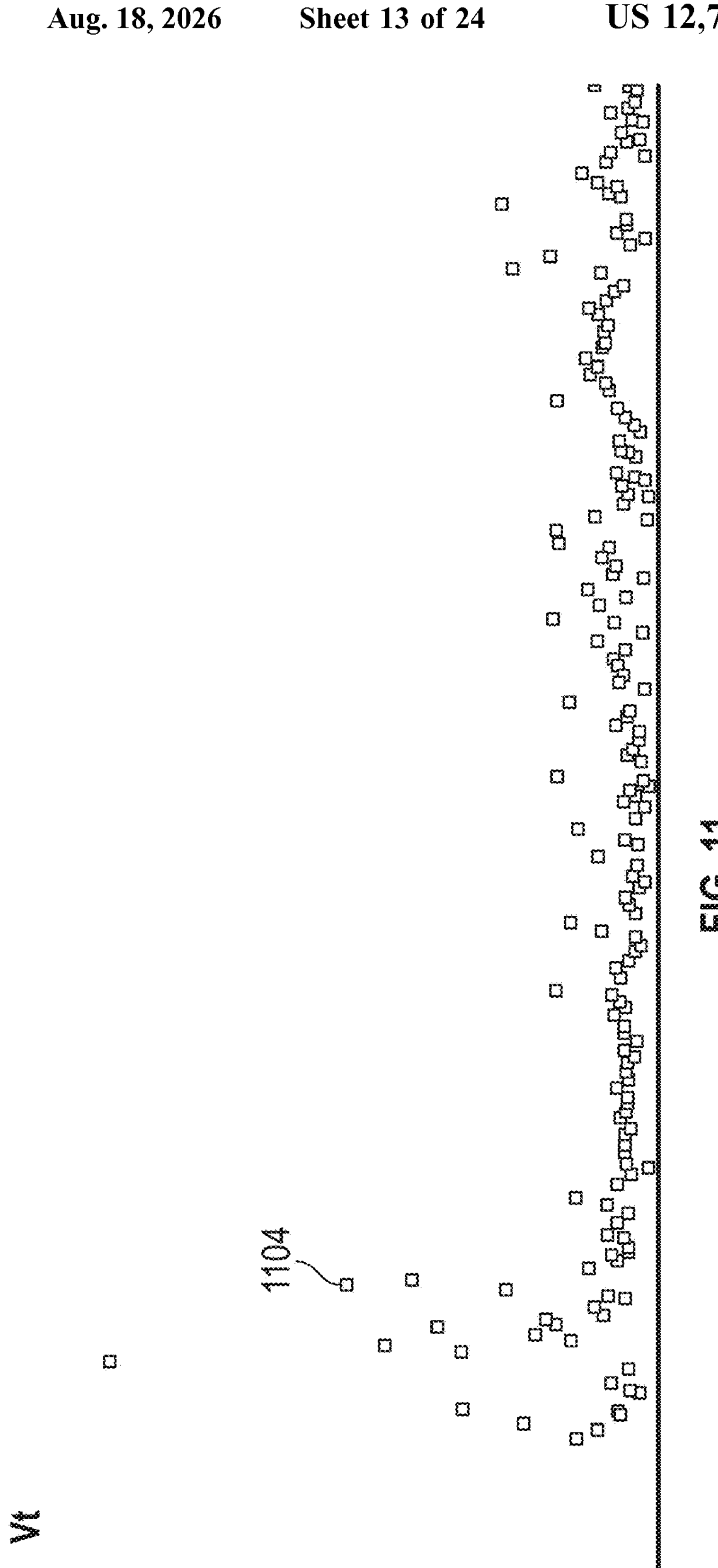
FIG. 11 is a magnified view of a portion of an example Tidal Volumes display in accordance with the present disclosure.

FIG. 11 is a magnified view 1102 of a portion of a Tidal Volumes display 608 for purposes of explanation. In FIG. 11, the x-axis corresponds to the time during the monitoring session of the user and the y-axis corresponds to Tidal Volume. The Tidal Volume for each breath cycle may be determined as described above for step 512. In the example illustrated, the Tidal Volume determination for each breath cycle may be plotted with a marker 1104 on the Tidal Volumes display 608/1102 along the x-axis at a time corresponding to the breath cycle. However, other graphical representations, such as a line graph or bar graph, may be used. The time corresponding to a given breath cycle may be the time at which the breath cycle began, the time at which the breath cycle ended, the time of the trough of the breath cycle, the time of the peak of the breath cycle, or any other suitable time within the breath cycle.

Figure 12:
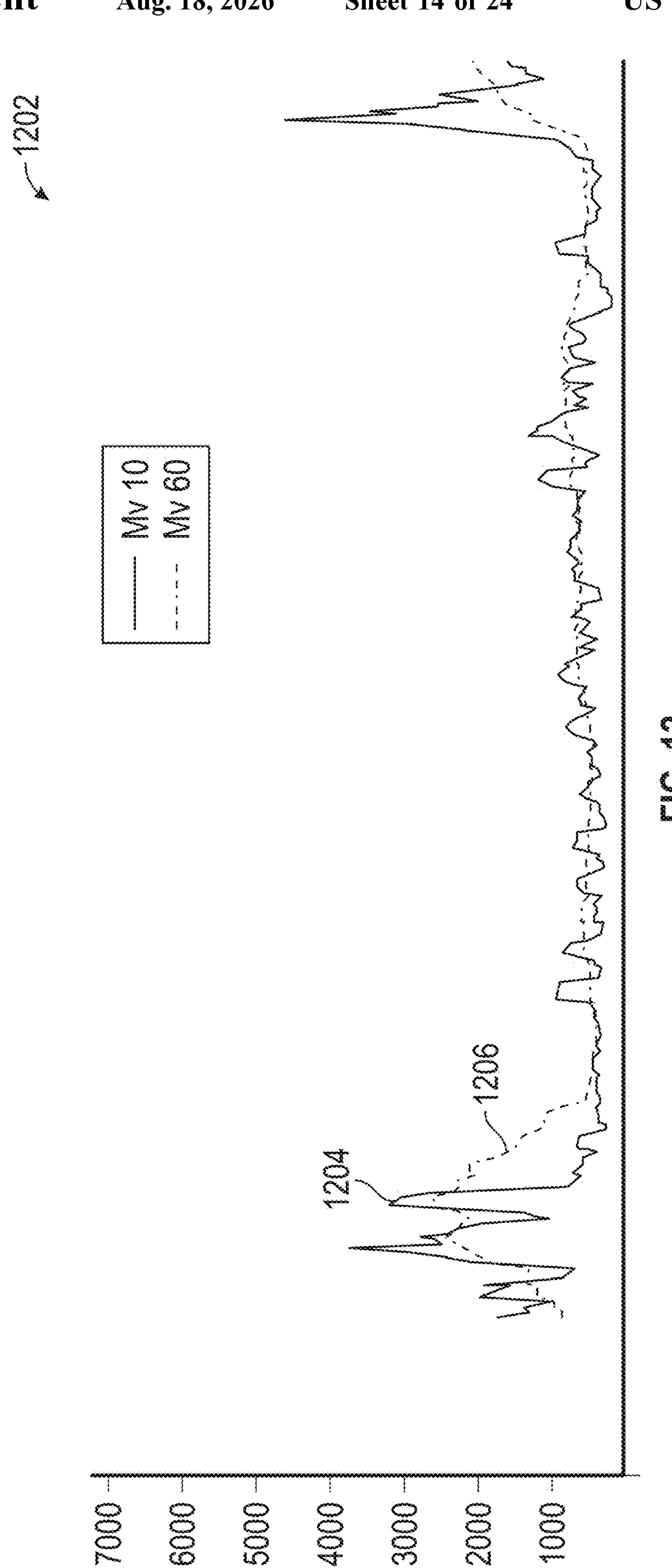
FIG. 12 is a magnified view of a portion of an example Minute Ventilation display in accordance with the present disclosure.

FIG. 12 is a magnified view 1202 of a portion of a Minute Ventilation display 610 for purposes of explanation. In FIG. 12, the x-axis corresponds to the time during the monitoring session of the user and the y-axis corresponds to Minute Ventilation. Minute Ventilation may be determined as described above for step 514. In the example illustrated, each Minute Ventilation determination may be plotted on the Minute Ventilation display 610/1202 at the corresponding time along the x-axis, and a line graph may be used to connect the Minute Ventilation determinations plotted. However, other graphical representations, such as a dot graph or bar graph, may be used. In an example embodiment, as shown, Minute Ventilations determined over different periods of time may be plotted on a single Minute Ventilation display 610/1202. For example, Minute Ventilation may be determined for 10 second periods normalized to 1 minute (Mv 10), as described above for step 514, and may be plotted 1204 as illustrated in FIG. 12. Additionally, for example, Minute Ventilation may be determined for 60 second periods (and normalized if needed) (Mv 60), as described above for step 514, and may also be plotted 1206 as illustrated in FIG. 12. Other or additional Minute Ventilation determinations over periods of time other than 10 seconds and 60 seconds may also be plotted on the Minute Ventilation display 610/1202.

Figure 13:
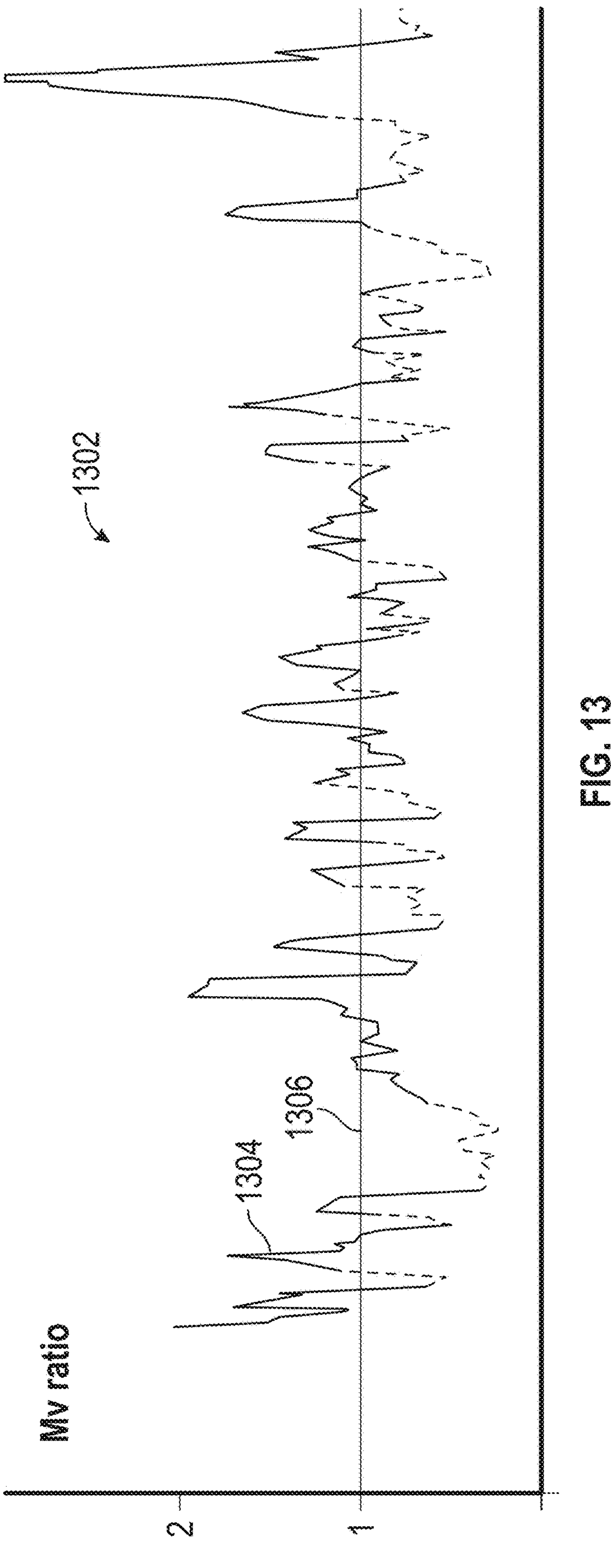
FIG. 13 is a magnified view of a portion of an example Minute Ventilation Ratio display in accordance with the present disclosure.

FIG. 13 is a magnified view 1302 of a portion of an My Ratio display 612 for purposes of explanation. In FIG. 13, the x-axis corresponds to the time during the monitoring session of the user and the y-axis corresponds to the value of the My Ratio. In an example, each My Ratio is determined by dividing an Mv 10 value, described above, by a corresponding Mv 60, also described above, corresponding to a given time during the monitoring session. Each My Ratio may then be plotted on the My Ratio display 612/1302 at the corresponding time along the x-axis, and a line graph 1304 may be used to connect the My Ratios plotted. However, other graphical representations, such as a dot graph or bar graph, may be used. While the My Ratio is described herein as Mv 10 divided by Mv 60, Minute Ventilation determinations over other suitable periods of time may be used to determine My Ratios. For example only, the My Ratio could be based on Minute Ventilation determined for 15 second periods normalized to 1 minute (Mv 15) and Minute Ventilation determined for 2 minute periods normalized to 1 minute (Mv 120), as described above for step 514, with the My Ratio determined as Mv 15 divided by Mv 120.

In some examples, an My Ratio of 1 may be used as a reference. In still further examples, a reference line 1306 at an My Ratio of 1 may be added to the My Ratio display 612/1302. As the My Ratio line goes above the reference ratio of 1 or above the reference ratio by some predetermined amount, the line may turn or start to turn to more of a first color, such as but not limited to, red, while as the My Ratio line drops below the reference ratio of 1 or below the reference ratio by some predetermined amount, such as but not limited to by about 0.3 (i.e., the My Ratio line drops below about 0.7), the line may turn or start to turn to more of a second color, such as but not limited to, blue, thereby providing a clearly visible representation or estimation of, for example, periods of oxygen desaturation.

Figure 14:
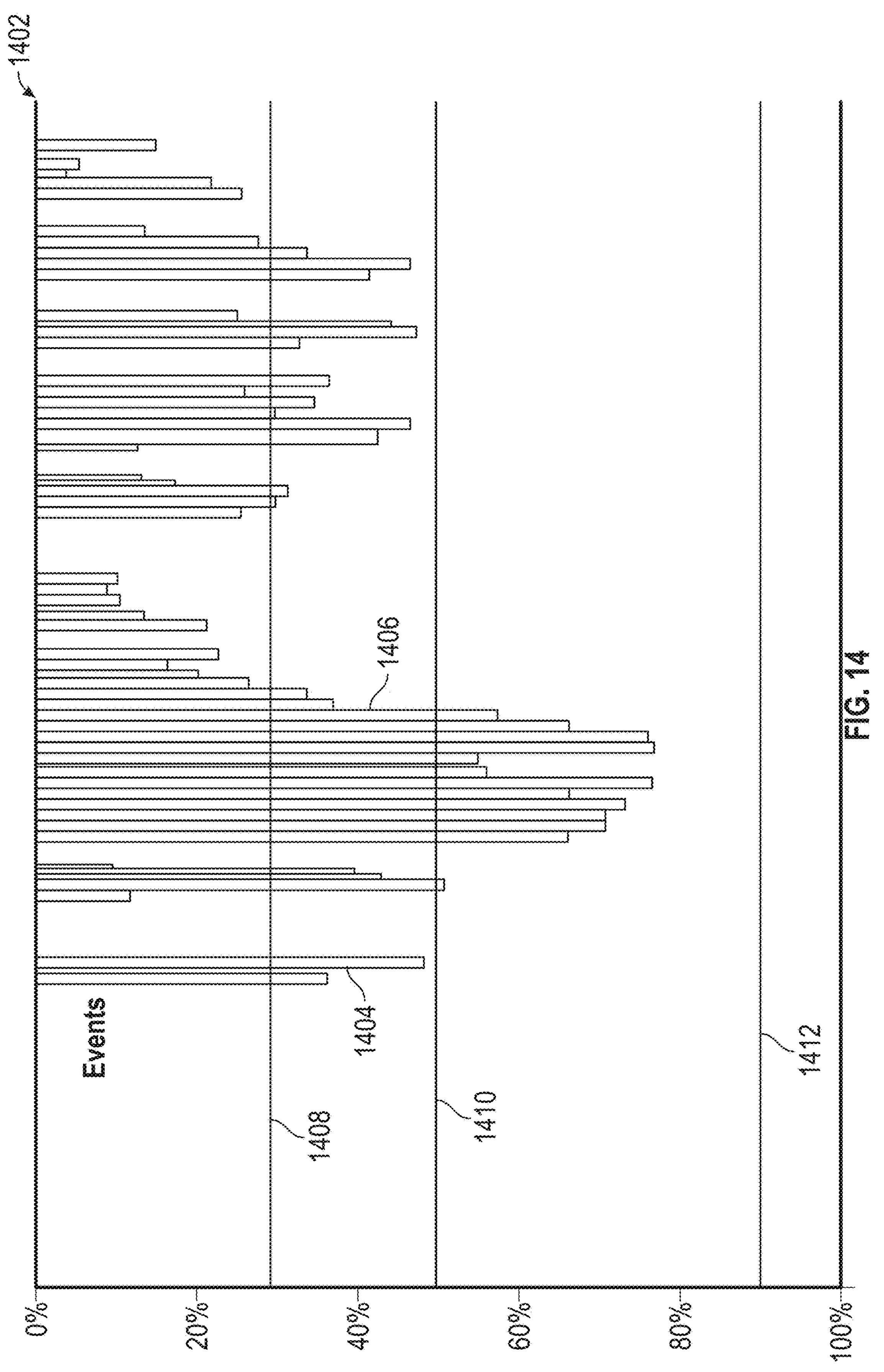
FIG. 14 is a magnified view of a portion of an example events display in accordance with the present disclosure.

FIG. 14 is a magnified view 1402 of a portion of an events display 614 for purposes of explanation. The events display 614/1402 visually represents respiratory instability events. In an example, a respiratory instability event 1404 is plotted when the My Ratio drops below the reference ratio of 1. The instability events may be plotted as a bar graph in which, as illustrated in FIG. 14, the x-axis corresponds to the time during the monitoring session of the user and the y-axis corresponds to the percentage that the My Ratio is below the reference ratio of 1. This percentage is also referred to herein as the instability severity. Each individual bar in the events display 614/1402 may generally correspond to a particular breath cycle, and immediately adjacent bars (e.g., where there is no gap or space between the bars) may all be considered a single instability event, such as instability event 1406 in FIG. 14. The width of a bar or aggregate of immediately adjacent bars corresponds to the length of time (or number of breath cycles) the instability event lasted. Using the data from the events display 1402, the number of instability events 1404 having an instability severity of any particular threshold of instability severity (e.g., 20%, 30%, 40%, etc.) or more may be determined with relative ease.

In some examples, instability severities of 30 and/or 50, or other suitable value, may be used as references. In still further examples, a reference line 1408 at an instability severity of 30 and/or a reference line 1410 at an instability severity of 50 may be added to the events display 1402. In another example, an instability severity of 90 may be used as a reference. A reference line 1412 at an instability severity of 90 may additionally or alternatively be added to the events display 1402. An instability severity of 90 may generally correspond to Apnea. However, the reference lines 1408, 1410, and/or 1412 may be located at a different instability severity or another reference line may be added at a different instability severity for analyzing other conditions.

Figure 15:
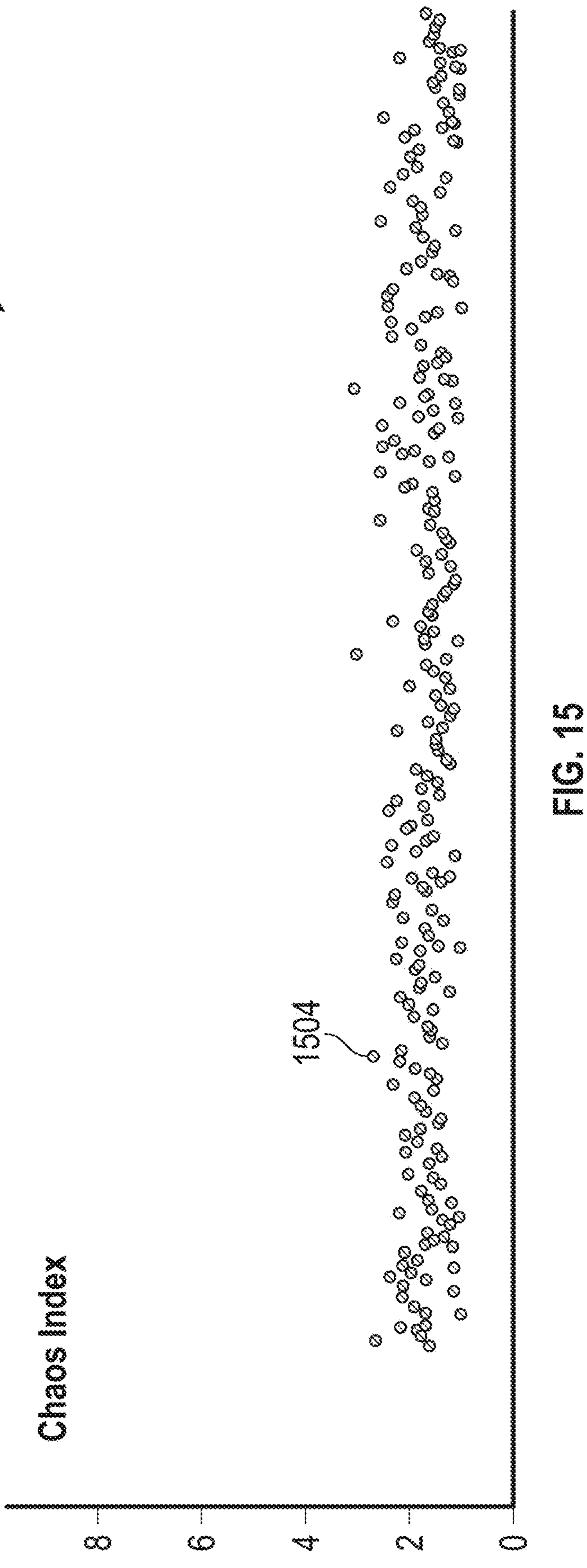
FIG. 15 is a magnified view of a portion of an example Chaos Index display in accordance with the present disclosure.

FIG. 15 is a magnified view 1502 of a portion of a Chaos Index display 616 for purposes of explanation. Generally, storing breath vectors 904, from which Tidal Volumes and Minute Ventilation can be determined and vice versa, rather than all the "raw" sensor data from which the breath vectors are based can take a significantly less amount of memory storage space. However, in doing so, the original "raw" sensor data and additional information that can be derived from such "raw" sensor data is lost. The Chaos Index, described in detail herein, may be used in place of the "raw" sensor data for certain indicators.

In general, the Chaos Index may be determined for any or each breath cycle and is a comparison of the breath vector of a breath cycle to the "raw" sensor data for the breath cycle. More specifically, determining a Chaos Index for a given breath cycle may include determining the total length (Lraw) of the curve passing through the "raw" sensor data collected or generated (e.g., from about 10 times per second to about 1000 times per second, as described above) during the breath cycle. Determining the Chaos Index for the given breath cycle may additionally include determining the total length vector length of the breath cycle (Lvector), which includes a sum of the length of the breath vector for the breath cycle and the length of an exhalation vector for the breath cycle that starts at the end point of the breath vector and ends at the starting point of the breath vector for the next successive breath cycle. The Chaos Index for the breath cycle may then be calculated as the ratio of Lraw to Lvector (e.g., Lraw divided by Lvector).

In the Chaos Index display 616/1502, the x-axis corresponds to the time during the monitoring session of the user and the y-axis corresponds to the value of the Chaos Index. In the example illustrated, the Chaos Index for each breath cycle may be plotted with a marker 1504 on the Chaos Index display 616/1502 along the x-axis at a time corresponding to the breath cycle. However, other graphical representations, such as a line graph or bar graph, may be used. The time corresponding to a given breath cycle may be the time at which the breath cycle began, the time at which the breath cycle ended, the time of the trough of the breath cycle, the time of the peak of the breath cycle, or any other suitable time within the breath cycle.

Typically, Lraw is around 2 to 2.5 times Lvector. However, when breathing is obstructed, Lraw may climb to upwards of 5 to 6 or more times Lvector. Accordingly, the Chaos Index may be used to detect paradoxical breathing and/or to help exclude or include certain conditions or indications when reviewing other metrics described herein. Additionally, the Chaos Index may be used to determine whether a ventilator patient is compliant with the ventilator. The right pressure level of a ventilator for each patient is different, and finding the right pressure level of a ventilator for a given patient can be an art form. If the pressure level is set properly, the patient breathes along with the ventilator and they are considered "compliant" with the ventilator. Often times, however, patients are not in compliance; they try to exhale but can't because the pressure is too high and, thus, they fight with the ventilator via extra muscular contractions or spasms, adding to the Chaos Index. The system 100 of the present disclosure may be used to monitor a ventilator patient, and the Chaos Index can help assist setting the right pressure level for the patient, as the closer that the Chaos Index is to 1, the more compliant they are with the ventilator.

Figure 16:
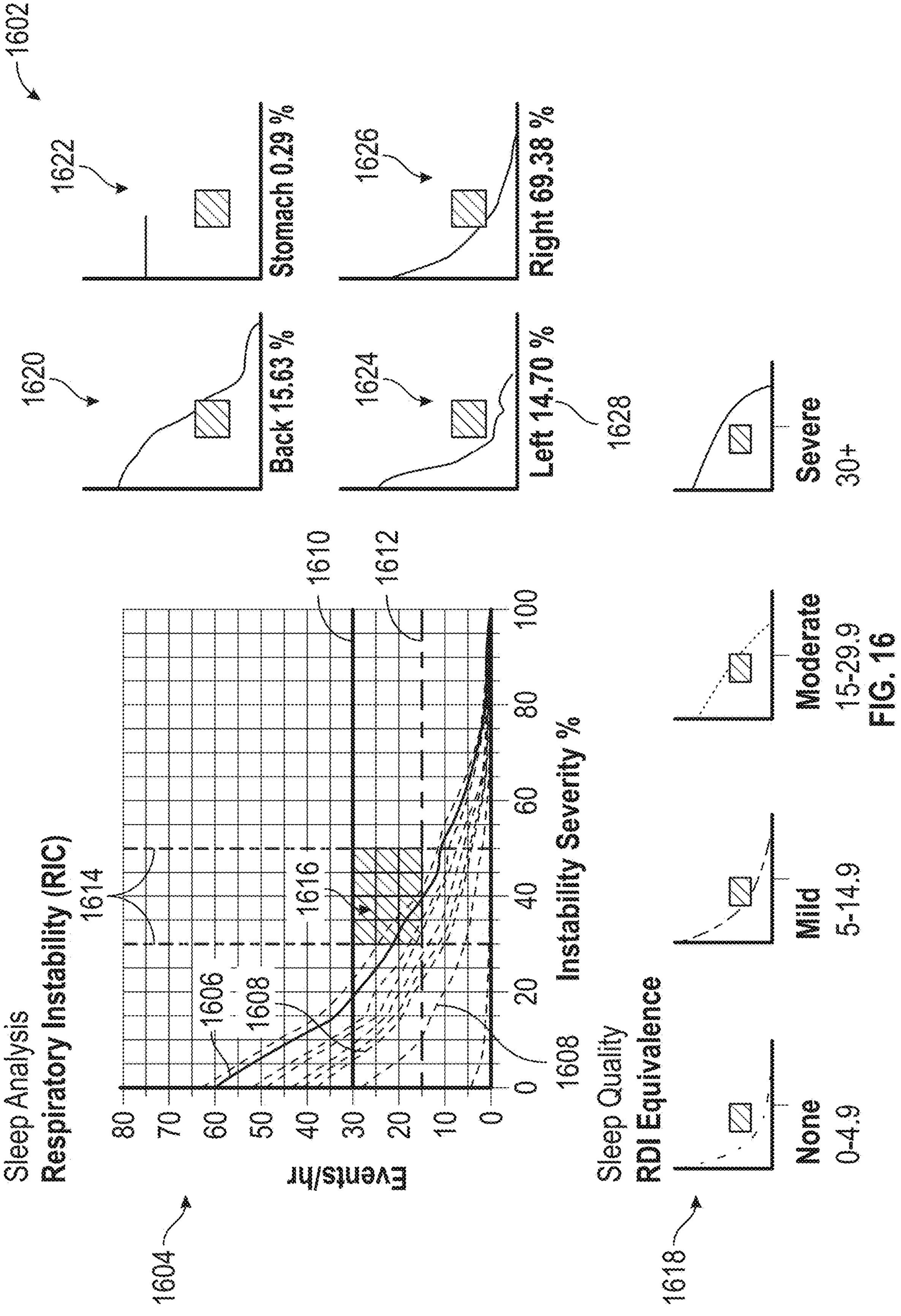
FIG. 16 is a magnified view of a portion of an example Respiratory Instability Curve display in accordance with the present disclosure.

FIG. 16 is a magnified view 1602 of a portion of an RIC display 618 for purposes of explanation. The RIC display 618/1602 may include a primary RIC 1604. The primary RIC 1604 generally illustrates the number of instability events per hour for various levels of instability severity. In the primary RIC 1604, the x-axis corresponds to the instability severity, in this case as a percentage from 0% to 100%, and the y-axis corresponds to the number of instability events per hour.

To generate the primary RIC 1604, the number of instability events 1404, determined as described above with respect to FIG. 14, having at least a particular instability severity threshold (e.g., 10%) occurring over the full monitoring session of the user are totaled and then divided by the number of hours corresponding to the full monitoring session (e.g., ~6.5 hours for the monitoring session corresponding to the example metrics and visual output 600 of FIG. 6) in order to obtain the number of instability events per hour at that instability severity threshold. This process may be repeated for a plurality of instability severity thresholds, such as 5%, 10%, 15%, 20%, 25%, 30%, 35%, 40%, 45%, 50%, 55%, 60%, 65%, 70%, 75%, 80%, 85%, 90%, 95%, and 100%. The number of instability severity thresholds for which the process may be repeated and/or the interval(s) between such instability severity thresholds can be as granular as desired. In the example illustrated, the number of instability events per hour determined for each desired or selected instability severity threshold may be plotted on the primary RIC 1604, and a line or curve 1606 may be used to connect the points plotted. However, other graphical representations, such as a dot graph or bar graph, may be used.

In the example primary RIC 1604 illustrated in FIG. 16, the thick, solid curve 1606 corresponds to the plotting of instability events that stayed below the reference ratio of 1 for at least 10 seconds. However, one or more plottings for instability events that stayed below the reference ratio of 1 for at least some other specified or predetermined period(s) of time may additionally or alternatively be illustrated, as demonstrated by the additional broken line curves 1608 in FIG. 16, each of which corresponds to a plotting of instability events that stayed below the reference ratio of 1 for at least a different specified or predetermined period of time.

In the primary RIC 1604, a horizontal reference line 1610, which may be displayed as a particular color such as red, may be provided at the 30 events per hour mark of the y-axis to quickly identify the instability severity thresholds of a particular curve (e.g., 1606, 1608) for which there are greater than 30 instability events per hour. Similarly, a horizontal reference line 1612, which may be displayed as another particular color such as yellow, may be provided at the 15 events per hour mark of the y-axis to quickly identify the instability severity thresholds of a particular curve (e.g., 1606, 1608) for which there are greater than 15 instability events per hour. Additionally, vertical reference lines 1614, which may be displayed as a particular color such as gray, may be provided at the 30% and 50% marks of the x-axis to quickly identify the number of instability events of a particular curve (e.g., 1606, 1608) having an instability severity of between about 30% and 50% (inclusive or exclusive of the 30% and 50% endpoints). In some examples, the area 1616 of the primary RIC 1604 bounded by reference lines 1610, 1612, and 1614 may be shaded or colored to highlight this area of significance.

The primary RIC 1604 may generally provide a visual identifier or predictor of respiratory instability with some general equivalence to the Respiratory Disturbance Index (RDI). For example, a legend 1618 illustrating how the primary RIC 1604 may compare to, or generally estimate or equate to, an RDI for the user may be provided in the RIC display 618/1602. As illustrated in legend 1618, in one example, an instability curve (e.g., 1606) that falls entirely below area 1616 may generally estimate or equate to an RDI of between about 0 and 4.9, an instability curve (e.g., 1606) that passes through the lower, left half of area 1616 may generally estimate or equate to an RDI of between about 5 and 14.9, an instability curve (e.g., 1606) that passes through the upper, right half of area 1616 may generally estimate or equate to an RDI of between about 15 and 29.9, and an instability curve (e.g., 1606) that falls entirely above area 1616 may generally estimate or equate to an RDI of 30 or greater. It is noted, however, that RDI as well as another commonly used index, the Apnea-Hypopnea Index (AHI), are determined generally by an oxygen desaturation of 3 or 4% in association with obstructed Apnea and Hypopnea. However, not all patients desaturate during respiratory instability. As such, RDI and AHI can often hide underlying health problems. The RIC of the present disclosure does not depend on blood oxygen monitoring, and therefore, can be more sensitive to revealing certain user/patient problems.

In addition to estimating the RDI, the shape (e.g., straight, convex, concave, etc.) of an instability curve (e.g., 1606) and/or where an instability curve crosses certain thresholds can also be indicative of one or more patient phenotypes of respiratory instability. In some example embodiments, the system 100 may determine such patient phenotypes automatically and may display the determined patient phenotypes in metrics/output 600.

In some example embodiments, the primary RIC 1604 or an alternative or additional RIC may be generated for a time period other than the entire monitoring session of the user. In some examples, the RIC display 1602 may include one or more RIC breakdowns for posture, such as one or more of an RIC breakdown 1620 for generally the time the user is predominantly on the user's back, an RIC breakdown 1622 for generally the time the user is predominantly on the user's stomach, an RIC breakdown 1624 for generally the time the user is predominantly on the user's left side, and an RIC breakdown 1626 for generally the time the user is predominantly on the user's right side. The instability curve or curves for each breakdown 1620, 1622, 1624, 1626 may be determined in the same manner as, for example, instability curves 1606, 1608, except that the curve or curves are determined over only the collective time periods for which the user is predominantly in the respective postural position. An indicator 1628 may be provided identifying the portion, in this case as a percentage, of the total time of the monitoring session that the user was predominantly in the respective postural position. In some examples, each of the RIC breakdowns 1620, 1622, 1624, 1626 may include any, some, or all of the features described with respect to the primary RIC 1604. RIC breakdowns 1620, 1622, 1624, 1626 can be particularly helpful, for example, in determining respiratory disturbances that are primarily related to specific postures (e.g., sleeping on the back). In such instances, it might be sufficient simply to use techniques that encourage the user or patient to avoid a particular posture (e.g., avoid sleeping on the user's back).

Figure 17:
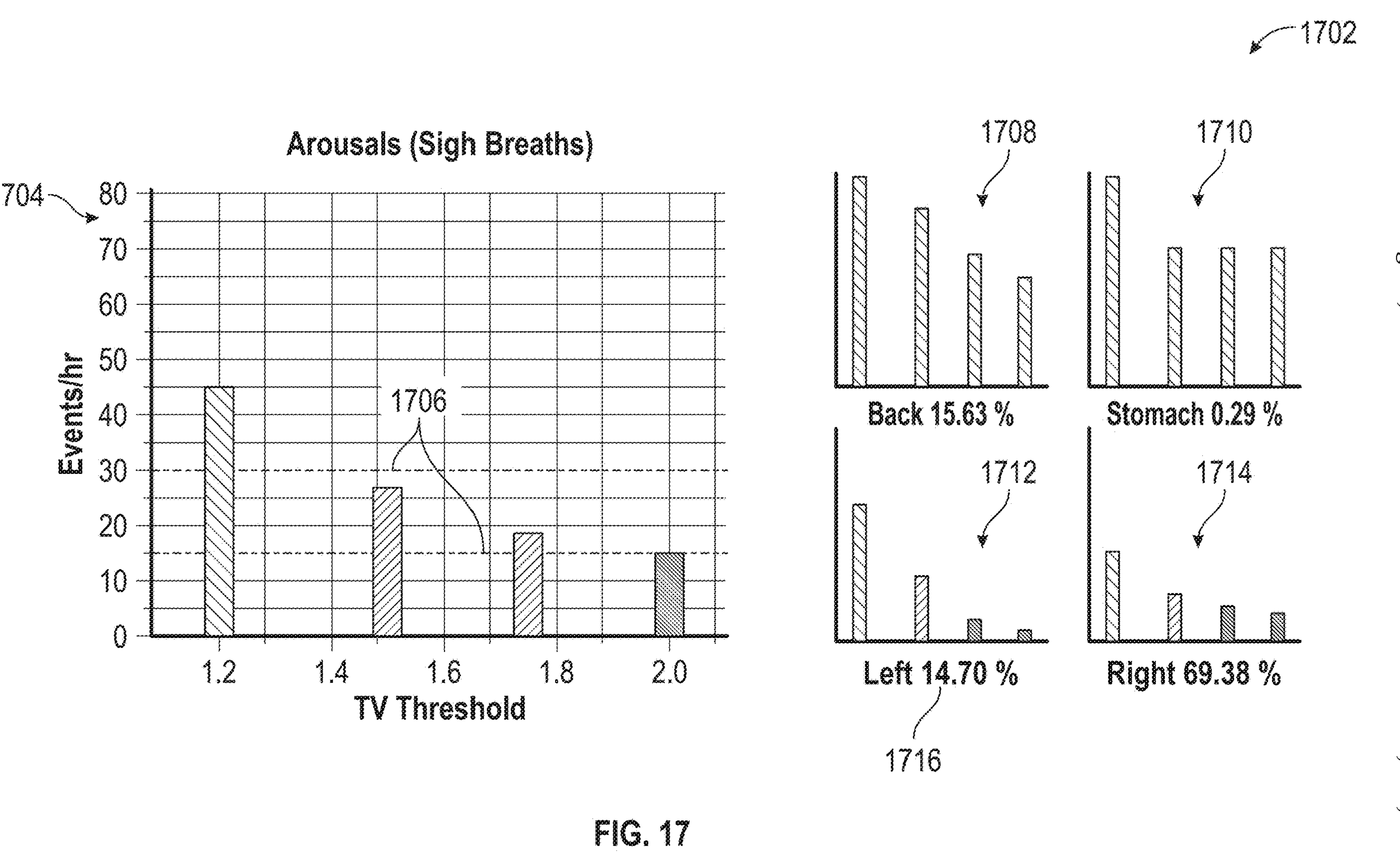
FIG. 17 is a magnified view of a portion of an example arousals display in accordance with the present disclosure.

FIG. 17 is a magnified view 1702 of a portion of an arousals display 620 for purposes of explanation. The arousals display 620/1702 may include a primary arousals graph 1704. Normally, when a user is asleep, the user's breathing is very stable, but if the user wakes up (e.g. arouses), there is often a larger, unexpected breath before the user goes back to sleep, which may be referred to herein as an arousal event. The primary arousals graph 1704 generally illustrates the number of such arousal events at a variety of such larger breath sizes. For the sake of clarity, the arousal events described with respect to the arousals display 620 are not the same as the events described with respect to the events display 614 or RIC display 618. In the primary arousals graph 1704, the x-axis corresponds to Tidal Volume threshold (TV Threshold), in this case as a ratio, and the y-axis corresponds to the number of arousal events per hour.

The TV Threshold generally corresponds to the relative size of the breath of a given breath cycle to the size of one or more of the breaths most recently preceding the given breath cycle. A TV Threshold may be determined for each breath cycle by dividing the Tidal Volume determined for the breath cycle, as described above, by the Tidal Volume determined for the most recently preceding breath cycle or by an average of the Tidal Volumes determined for two or more of the most recently preceding breath cycles or by an average of the Tidal Volumes determined over a preceding period of time, such as the preceding 15, 30, 45, or 60 seconds. Then, for each of one or more TV Thresholds, such as 1.2, 1.5, 1.75, and 2.0, the number of breath cycles throughout the monitoring session having at least that TV Threshold are totaled and then divided by the number of hours corresponding to the full monitoring session (e.g., ~6.5 hours for the monitoring session corresponding to the example metrics and visual output 600 of FIG. 6) in order to obtain the number of arousal events per hour having that TV Threshold. The number of TV Thresholds for which this process may be repeated and/or the interval(s) between such TV Thresholds can be as granular as desired. In the example illustrated, the number of arousal events per hour determined for each desired or selected TV Threshold may be plotted on the primary arousals graph 1704 as a bar graph. However, other graphical representations, such as a dot graph or line graph, may be used. In the primary arousals graph 1704, horizontal reference lines 1706, which may each be displayed as a particular color such as red, yellow, or gray, may be provided at the 30 and 15 events per hour marks of the y-axis to quickly identify the TV Thresholds for which there are greater than 30 and 15, respectively, arousal events per hour. In some examples, the bars may be colored according to their height. For example, and not limited to, a bar extending above the reference line 1706 at the 30 events per hour mark of the y-axis may be colored red, a bar extending above the reference line 1706 at the 15 events per hour mark of the y-axis but not to the reference line at the 30 events per hour mark of the y-axis may be colored yellow, and a bar ending below the reference line 1706 at the 15 events per hour mark of the y-axis may be colored green.

In some example embodiments, the primary arousals graph 1704 or an alternative or additional arousals graph may be generated for a time period other than the entire monitoring session of the user. In some examples, the arousals display 1702 may include one or more arousal graph breakdowns for posture, such as one or more of an arousal graph breakdown 1708 for generally the time the user is predominantly on the user's back, an arousal graph breakdown 1710 for generally the time the user is predominantly on the user's stomach, an arousal graph breakdown 1712 for generally the time the user is predominantly on the user's left side, and an arousal graph breakdown 1714 for generally the time the user is predominantly on the user's right side. The arousal graphs for each breakdown 1708, 1710, 1712, 1714 may be determined in the same manner as, for example, arousal graph 1704, except that the bars (or other graphical representations) are determined over only the collective time periods for which the user is predominantly in the respective postural position. An indicator 1716 may be provided identifying the portion, in this case as a percentage, of the total time of the monitoring session that the user was predominantly in the respective postural position. In some examples, each of the arousal graph breakdowns 1708, 1710, 1712, 1714 may include any, some, or all of the features described with respect to the primary arousal graph 1704.

Figure 18:
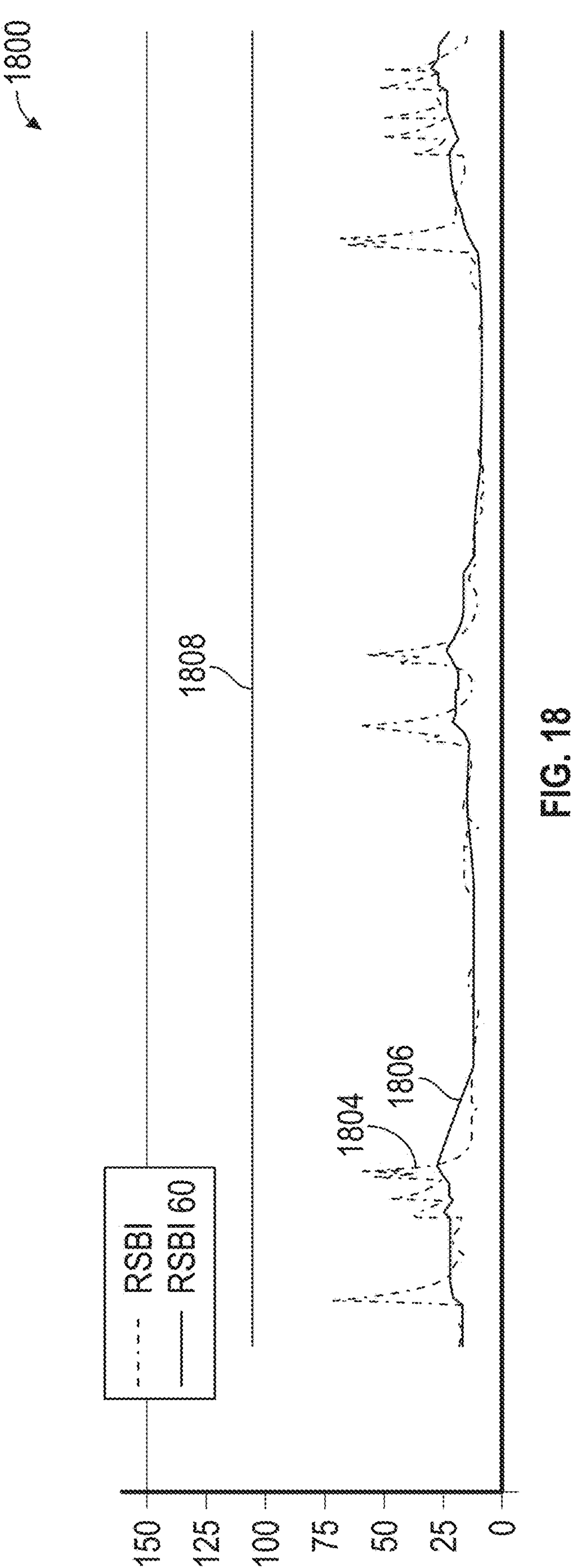
FIG. 18 is a magnified view of a portion of an example Rapid Shallow Breathing Index display in accordance with the present disclosure.

In some example embodiments, the metrics/output 600 may also include a Rapid Shallow Breathing Index (RSBI) display 1800, a portion of which is illustrated in magnified form in FIG. 18 for purposes of explanation. As with any other of the metrics/output 600, the RSBI may be determined at various periodic or non-periodic times throughout an entire monitoring session or may be determined at various periodic or non-periodic times throughout smaller portions or chunks of time of the monitoring session, such as 30-minute chunks or any other suitably sized chunks, such as 5-minute, 6-minute, 10-minute, 15-minute, 20-minute chunks, or the like.

The RSBI display 1800 can be used to determine whether a ventilator patient can survive off the ventilator. The RSBI display 1800 can also provide a good indicator of whether the user is snoring.

In FIG. 18, the x-axis corresponds to the time during the monitoring session of the user and the y-axis corresponds to the value of the RSBI. In an example, each RSBI is determined by dividing an RR value, described above, by a corresponding Tidal Volume, also described above, corresponding to a given time during the monitoring session. Each RSBI may then be plotted on the RSBI display 1800 at the corresponding time along the x-axis, and a line graph 1804 may be used to connect the RSBIs plotted. However, other graphical representations, such as a dot graph or bar graph, may be used.

Figure 19:
FIG. 19 is a magnified view of a portion of an example vector slope display in accordance with the present disclosure.
Figure 19:
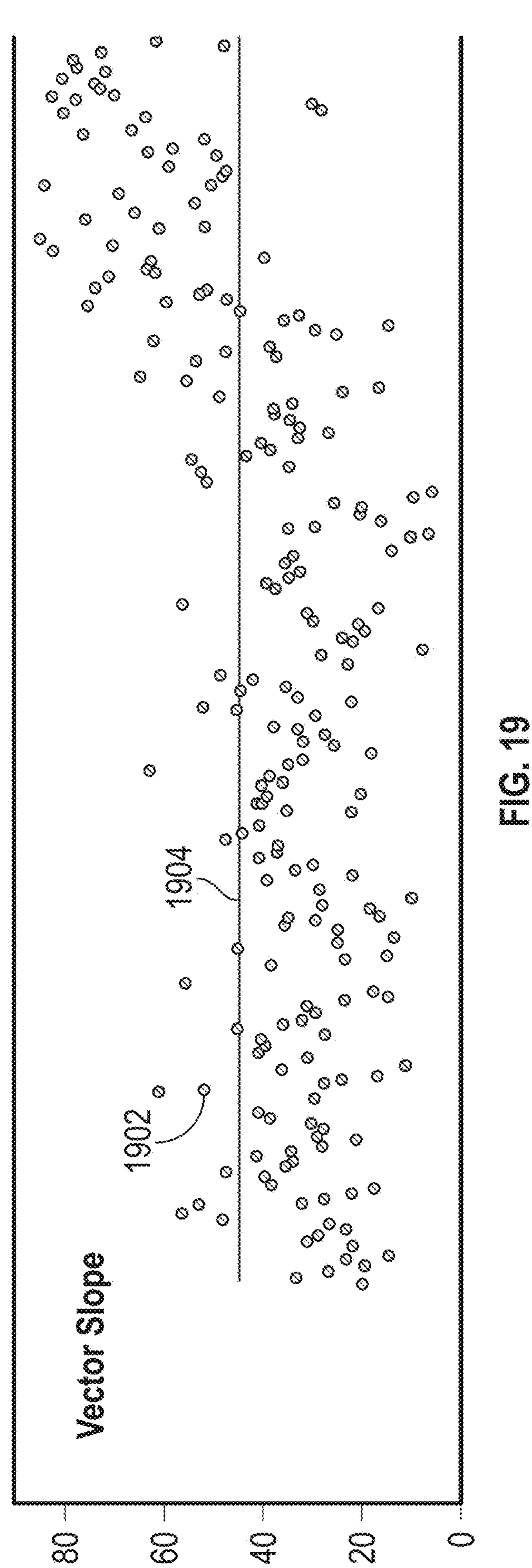

In addition to RSBI, an average RSBI may be plotted. The average RSBI, which may be referred to herein as RSBI x, generally corresponds to an average RSBI over a predetermined time period x, such as 30 seconds, 60 seconds, 120 seconds, etc. An RSBI x value may be determined, in an example, by averaging the RSBI values over the predetermined time period x, such as the immediately preceding period of time x. In another example, an RSBI x value may be determined by dividing an average of the RR values over the predetermined time period x, such as the immediately preceding period of time x, and by an average of Tidal Volumes over the corresponding period of time x. Each RSBI x value may then be plotted on the RSBI display 1800 at the corresponding time along the x-axis, and a line graph 1806 may be used to connect the RSBI x values plotted. However, other graphical representations, such as a dot graph or bar graph, may be used. FIG. 19 illustrates an example of RSBI 60 that has been plotted, corresponding to RSBI x values, determined as described above, wherein the predetermined time period x is 60 seconds. However, any other suitable time period may be used for determining an RSBI x and plotting an RSBI x graph.

In some examples, an RSBI of 105, or other suitable value, may be used as a reference. In still further examples, a reference line 1808 at an RSBI of 105 may be added to the RSBI display 1800. An RSBI of less than 105 is often considered a threshold value representing when a patient is or likely should be able to survive without ventilation support. However, the reference line 1808 may be located at a different RSBI or another reference line may be added at a different RSBI for analyzing other conditions.

In some example embodiments, the metrics/output 600 may also include a vector slope display 1900, a portion of which is illustrated in magnified form in FIG. 19 for purposes of explanation. As with any other of the metrics/output 600, vector slope may be determined at various periodic or non-periodic times throughout an entire monitoring session or may be determined at various periodic or non-periodic times throughout smaller portions or chunks of time of the monitoring session, such as 30-minute chunks or any other suitably sized chunks, such as 5-minute, 6-minute, 10-minute, 15-minute, 20-minute chunks, or the like. Vector slope for any given breath and/or trends in vector slopes for sequences of breaths can be fairly indicative of obstructive breathing patterns.

In FIG. 19, the x-axis corresponds to the time during the monitoring session of the user and the y-axis corresponds to an angle value. Each vector slope corresponds to the incline angle of a corresponding breath vector, described above, relative the x-axis of the breath vectors display 604/902. In an example, each vector slope may be determined by determining the slope, s, of a corresponding breath vector during the monitoring session and then calculating the corresponding incline angle, for example, using the equation arctan(s). Each vector slope may then be plotted with a marker 1902 on the vector slope display 1900 at the corresponding time along the x-axis. However, other graphical representations, such as a line graph or bar graph, may be used.

In some examples, a vector slope of 45, or other suitable value, may be used as a reference. In still further examples, a reference line 1904 at a vector slope of 45 may be added to the vector slope display 1900. A vector slope of around 45 generally corresponds to a relatively normal and relaxed inhalation flow rate. However, the reference line 1904 may be located at a different vector slope or another reference line may be added at a different vector slope for analyzing other conditions.

Figure 20:
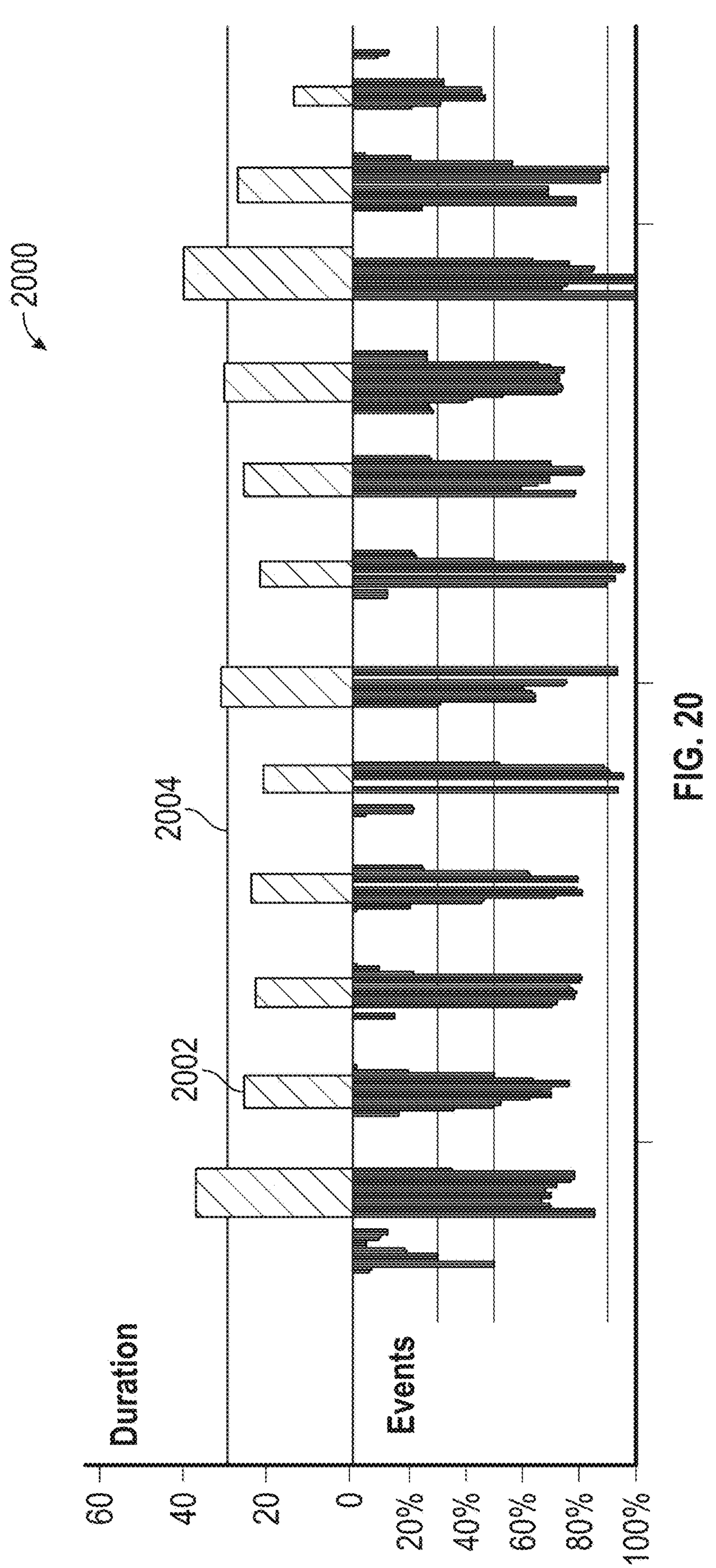
FIG. 20 is a magnified view of a portion of an example event duration display in accordance with the present disclosure.

In some example embodiments, the metrics/output 600 may also include an event duration display 2000, a portion of which is illustrated in magnified form in FIG. 20 for purposes of explanation. As with any other of the metrics/output 600, event durations may be determined at various periodic or non-periodic times throughout an entire monitoring session or may be determined at various periodic or non-periodic times throughout smaller portions or chunks of time of the monitoring session, such as 30-minute chunks or any other suitably sized chunks, such as 5-minute, 6-minute, 10-minute, 15-minute, 20-minute chunks, or the like. While the event duration display 2000 may be generated and displayed separately and without the events display, the event duration display 2000 may, in an example, be displayed adjacent to the events display 614/1402, as illustrated in FIG. 20.

The event duration display 2000, in general, visually represents instability events, as described above, that last at least a predetermined amount of time (e.g., 5 seconds, 10 seconds, 20 seconds, etc.) and have at least a particular instability severity (e.g., 20%, 30%, 40%, etc.). While any predetermined amount of time or instability severity may be selected, in an example, event duration display 2000 visually represents instability events that last at least 10 seconds and have an instability severity of at least 30%. In the event duration display 2000 of FIG. 20, the x-axis corresponds to the time during the monitoring session of the user and the y-axis corresponds to the duration of an instability event in seconds. For an instability event, as described above, meeting the aforementioned time and instability severity thresholds, a bar 2002 may be plotted in the event duration display 2000 at the time during the monitoring session corresponding to that instability event. The height of the bar 2002 represents the duration (e.g., in seconds) of the instability event. Of course, other graphical representations, such as a line graph or dot graph, may be used. In the example illustrated, the duration of the instability event can also be represented by the width of the bar 2002 along the x-axis.

In some examples, a duration of 30 seconds, or other suitable value, may be used as a reference. In still further examples, a reference line 2004 at a duration of 30 seconds may be added to the event duration display 2000. However, the reference line 2004 may be located at a different duration values or another reference line may be added at a different duration value. The event duration display 2000 can help a doctor quickly correlate how instability events are distributed throughout the monitoring session and/or whether instability events are posture related or related to REM sleep, which can help the doctor characterize the phenotype of the user or patient and can contribute to the doctor's decision on how to proceed with the user or patient.

Figure 21:
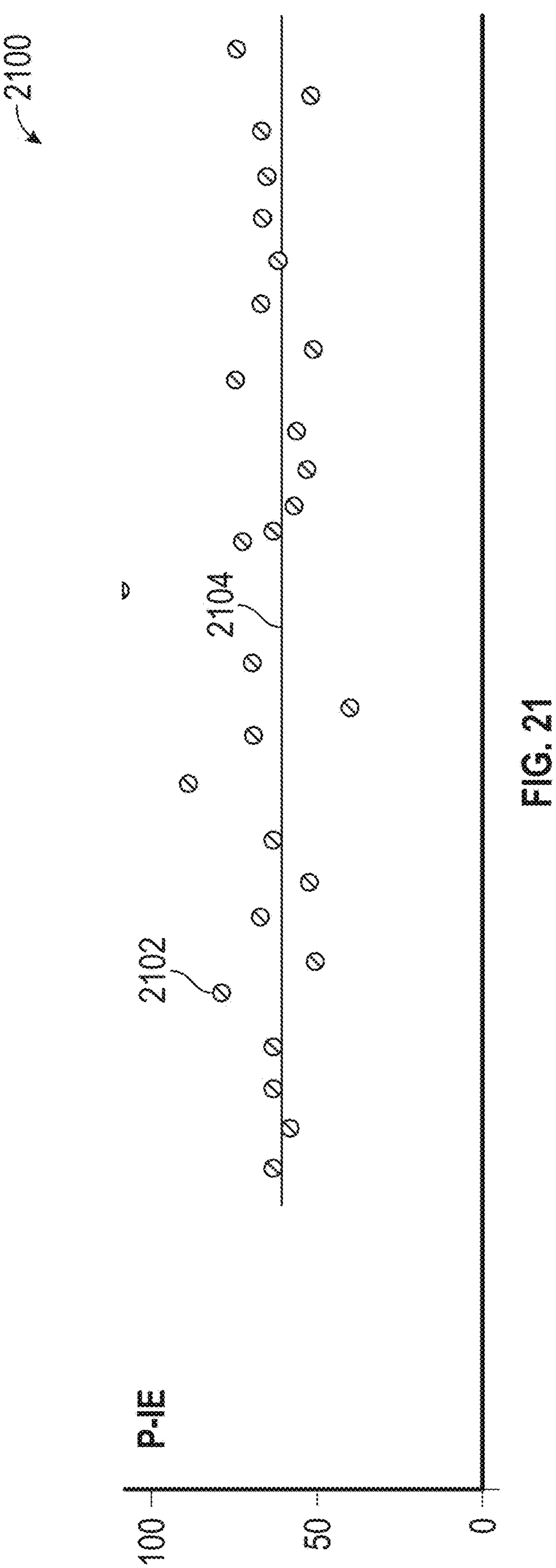
FIG. 21 is a magnified view of a portion of an example Period of time between Instability Events display in accordance with the present disclosure.
Figure 22:
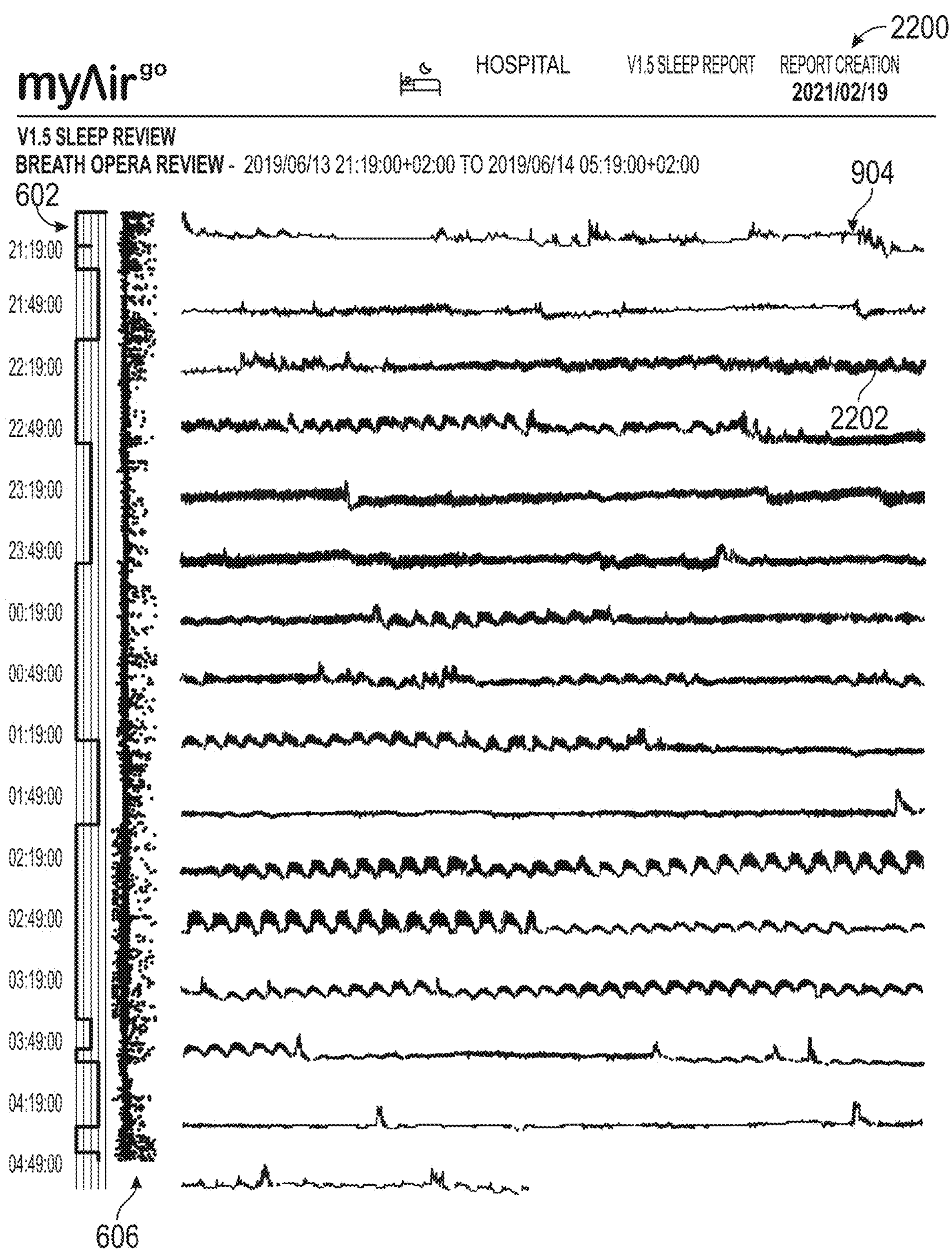
FIG. 22 is a magnified view of a portion of an example quick analysis display in accordance with the present disclosure.

In some example embodiments, the metrics/output 600 may also include a Period of time between Instability Events (P-IE) display 2100, a portion of which is illustrated in magnified form in FIG. 21 for purposes of explanation. As with any other of the metrics/output 600, P-IEs may be determined at various periodic or non-periodic times throughout an entire monitoring session or may be determined at various periodic or non-periodic times throughout smaller portions or chunks of time of the monitoring session, such as 30-minute chunks or any other suitably sized chunks, such as 5-minute, 6-minute, 10-minute, 15-minute, 20-minute chunks, or the like.

The P-IE display 2100, in general, visually illustrates the period of time between adjacent instability events, as described above, that last at least a predetermined amount of time (e.g., 5 seconds, 10 seconds, 20 seconds, etc.) and have at least a particular threshold of instability severity (e.g., 20%, 30%, 40%, etc.). While any predetermined amount of time or threshold of instability severity may be selected, in an example, P-IE display 2100 visually illustrates the period of time between adjacent instability events that last at least 10 seconds and have a threshold of instability severity of at least 30%. A P-IE may be measured as the time between the beginnings of adjacent instability events, the time between the ends of adjacent instability events, the time between the beginning of a first one of the adjacent instability events and the end of a second one of the adjacent instability events, the time between the end of a first one of the adjacent instability events and the beginning of a second one of the adjacent instability events, or the time between any other suitable portion a first one of the adjacent instability events and any other suitable portion of a second one of the adjacent instability events. As illustrated in FIG. 21, each P-IE is measured as the time between the beginnings of adjacent instability events. In the P-IE display 2100 of FIG. 21, the x-axis corresponds to the time during the monitoring session of the user and the y-axis corresponds to the value of the P-IE, for example, in seconds. Each P-IE may be plotted with a marker 2102 on the P-IE display 2100 at the corresponding time along the x-axis. However, other graphical representations, such as a line graph or bar graph, may be used.

In some examples, a P-IE of 60 seconds, or other suitable value, may be used as a reference. In still further examples, a reference line 2104 at a P-IE of 60 seconds may be added to the P-IE display 2100. However, the reference line 2104 may be located at a different P-IE values or another reference line may be added at a different P-IE value. The P-IE display 2100 can be useful, because in the case of periodic breathing (such as Cheyne Stokes), this graph visually illustrates a consolidation of values over the period of time that the user or patient is breathing periodically. In other circumstances where the instability events are not periodic, the P-IE display 2100 will appear somewhat chaotic/random.

In some example embodiments, the metrics/output 600 may also include a quick analysis display 2200, which is generally a combination of multiple of the metrics or output described above. The quick analysis display 2200 may include the breath vectors 904, determined as described above, for a portion or all of the monitoring session in one or more rows. In the quick analysis display 2200, the end point of each breath vector (generally with the exception of the last breath vector of the monitoring session and potentially one or more of the last vectors of each row) may additionally be connected by a vector to the starting point of the next successive breath vector, to form a generally continuous waveform 2202 (broken up generally only due to the separation of the waveform into rows due to space limitations). For each given time or time period along the waveform 2202, the waveform may be colored, however, pursuant to the coloring of the My Ratio line, determined as described above, at the corresponding time or time period. For quick and easy reference, the RR display 606 and position indicator 602 (in this case, in the form of position indicator 806) for the same time period as used for the waveform 2202 may be provided in respective rows that are generally or substantially perpendicular to the rows of the waveform 2202.

One or more of the foregoing metrics/output 600 described above may be used to characterize certain breathing patterns of the user. For example, the inhalation times and exhalation times of the user at rest may be used as a diagnostic indication of bronchial congestion, as it generally takes longer to exhale when congested. Fragmented breath vectors can be indicative that the user is snoring, both during inhalation and exhalation. A pattern and/or distribution of fragmented breath vectors are generally easy to visually recognize from, for example, the breath vectors display 604. Progressive vertical movement of successive breath vectors in, for example, the breath vectors display 604 can be indicative of metabolic and/or sleep stage changes. Sudden vertical displacement of a series of breath vectors can be indicative of obstruction, during which the breath vectors indicate flow between the upper and lower lobes of the lungs, generally without flow out of the mouth and nose (e.g., there is no effective breathing, just movement of air between the upper and lower lobes of the lungs). One or more of the foregoing metrics/output 600 can generally be used to identify any periodic or repetitive breathing patterns, such as but not limited to, central apnea, central hypopnea, obstructive apnea, obstructive hypopnea, Cheynee-Stokes, Kussmaul, hyperinflation, and hypoinflation, each indicative of a clinically relevant diagnosis. Relevant breath vector progressions can be identified from, for example, the breath vectors display 604 as patterns over time observed in the low points of the breath vectors, the high points of breath vectors, the average height of the vectors, the average size of the breath vector, etc. Various combinations of these patterns can be indications for various metabolic and cognitive states or central nervous system disorders.

One or more of the foregoing metrics/output 600 described above may be used to identify breathing patterns indicative of various stages of sleep, such as falling asleep, awakening, and various sleep states N1-N3, REM sleep, and wake. For example, falling asleep may be evidenced by a sequence of 5-10 breaths wherein each exhale (e.g., the vertical distance between the end point of a breath vector to the starting point of the next breath vector) is larger than the subsequent inhale (e.g., the length of a breath vector), leading to a progressive "deflation" of the lungs (known as a lowered FRC). Essentially, this may be exhibited in the breath vectors display as a progressive downward movement of the breath vectors. Awakening may be evidenced by an inhalation which is unexpectedly larger than a certain number of previous breaths (e.g., a "gasp"). In the breath vectors display 604, such a breath vector stands out from the other breath vectors in a group. Sleep states N1 and N3 may be evidenced by slow progressive migrations of average girth size up or down (i.e., progressive migrations of breath vectors up or down), together with similarly slow progressions of Tidal Volume up or down. Sleep State N2 may be evidenced by a sequence of very regular breathing with no girth (e.g., breath vector) migrations up or down. REM sleep may be evidenced by a highly, seemingly randomly, fluctuating respiratory rate, which is in general, slightly faster than in the other sleep states. Wake may be evidenced by a similarly random, slightly faster respiratory rate like in REM, together with a generally larger average girth (e.g., height of the breath vectors in the breath vectors display 604).

One or more of the foregoing metrics/output 600 may additionally or alternatively be used as inputs to a trained machine learning or deep learning model, trained with actual patient data, to automatically characterize breathing patterns of the user or automatically determine or estimate other metrics for the user, such as sleep states (wake, N1, N2, N3, REM), an actual RDI, Apnea-Hypopnea Index (AHI), or Sleep Disturbance Index (SDI).

ADDITIONAL EXAMPLES

Example 1 includes subject matter relating to a computer readable storage medium comprising instructions, that when executed by one or more processors, carry out operations comprising: receiving raw sensor data from a monitoring device worn by a user, the raw sensor data corresponding to girth measurements relating to a torso of the user; determining first minute ventilation data for a plurality of times during a monitoring session of the user based on the raw sensor data, the first minute ventilation data for a given time of the plurality of times determined by aggregating tidal volumes for a series of breath cycles completed within a first specified time range corresponding to the given time and normalizing to one minute; determining second minute ventilation data for the plurality of times during the monitoring session of the user based on the raw sensor data, the second minute ventilation data for a given time of the plurality of times determined by aggregating tidal volumes for a series of breath cycles completed within a second specified time range corresponding to the given time and normalizing to one minute; determining a minute ventilation ratio for each of the plurality of times, wherein the minute ventilation ratio for a given time is determined by dividing the first minute ventilation data corresponding to the given time by the second minute ventilation data corresponding to the given time; and identifying minute ventilation ratios that are below a specified reference ratio as instability events.

In Example 2, the subject matter of Example 1 optionally includes wherein the instructions carry out further operations comprising plotting the instability events on an instability event graph, the instability event graph having a first axis representing time and a second axis corresponding to instability severity, wherein instability severity for a given instability event is determined as an amount that the minute ventilation ratio corresponding to the instability event is below the specified reference ratio.

In Example 3, the subject matter of Example 1 or 2 optionally includes wherein the first specified time range is 10 seconds and the second specified time range is 60 seconds.

In Example 4, the subject matter of any of Examples 1 to 3 optionally includes wherein the specified reference ratio is 1.

In Example 5, the subject matter of any of Examples 1 to 4 optionally includes wherein the instructions carry out further operations comprising determining a number of instability events per hour for a given instability severity threshold by dividing a number of instability events during the monitoring session having an instability severity equal to or greater than the given instability severity threshold by an amount of time corresponding to the monitoring session, wherein instability severity for a given instability event is determined as an amount that the minute ventilation ratio corresponding to the instability event is below the specified reference ratio.

In Example 6, the subject matter of Example 5 optionally includes wherein the instructions carry out further operations comprising repeating the operation of determining a number of instability events per hour for a given instability severity threshold for each of a plurality of instability severity thresholds to determine a number of instability events per hour for each of the plurality of instability severity thresholds.

In Example 7, the subject matter of Example 6 optionally includes wherein the instructions carry out further operations comprising plotting the number of instability events per hour for each of the plurality of instability severity thresholds on a respiratory instability graph, the respiratory instability graph having a first axis corresponding to instability severity and a second axis corresponding to a number of instability events per hour.

In Example 8, the subject matter of Example 7 optionally includes wherein plotting the number of instability events per hour for each of the plurality of instability severity thresholds on a respiratory instability graph comprises plotting a line passing through the plotted number of instability events per hour for the plurality of instability severity thresholds.

In Example 9, the subject matter of Example 7 or 8 optionally includes wherein plotting the number of instability events per hour for each of the plurality of instability severity thresholds on a respiratory instability graph comprises plotting reference lines bounding an area of the respiratory instability graph between a first number of instability events per hour and a second number of instability events per hour and between a first instability severity and a second instability severity.

In Example 10, the subject matter of Example 9 optionally includes wherein the first number of instability events per hour is about 15, the second number of instability events per hour is about 30, the first instability severity is about 30%, and the second instability severity is about 50%.

In Example 11, the subject matter of any of Examples 1 to 4 optionally includes wherein the instructions carry out further operations comprising determining a number of instability events per hour for a given instability severity threshold for a specified user position by dividing a number of instability events during portions of the monitoring session in which the user is determined to be in the specified user position having an instability severity equal to or greater than the given instability severity threshold by an amount of time during the monitoring session in which the user is determined to be in the specified user position, wherein instability severity for a given instability event is determined as an amount that the minute ventilation ratio corresponding to the instability event is below the specified reference ratio.

In Example 12, the subject matter of Example 11 optionally includes wherein the instructions carry out further operations comprising repeating the operation of determining a number of instability events per hour for a given instability severity threshold for a specified user position for each of a plurality of instability severity thresholds to determine a number of instability events per hour for each of the plurality of instability severity thresholds.

In Example 13, the subject matter of Example 12 optionally includes wherein the instructions carry out further operations comprising plotting the number of instability events per hour for each of the plurality of instability severity thresholds on a respiratory instability graph, the respiratory instability graph having a first axis corresponding to instability severity and a second axis corresponding to a number of instability events per hour.

In Example 14, the subject matter of Example 13 optionally includes wherein plotting the number of instability events per hour for each of the plurality of instability severity thresholds on a respiratory instability graph comprises plotting a line passing through the plotted number of instability events per hour for the plurality of instability severity thresholds.

In Example 15, the subject matter of Example 13 or 14 optionally includes wherein plotting the number of instability events per hour for each of the plurality of instability severity thresholds on a respiratory instability graph comprises plotting reference lines bounding an area of the respiratory instability graph between a first number of instability events per hour and a second number of instability events per hour and between a first instability severity and a second instability severity.

In Example 16, the subject matter of Example 15 optionally includes wherein the first number of instability events per hour is about 15, the second number of instability events per hour is about 30, the first instability severity is about 30%, and the second instability severity is about 50%.

In Example 17, the subject matter of any of Examples 1 to 16 optionally includes wherein the instructions carry out further operations comprising: determining a period of time between adjacent instability events (P-IE) that last for at least a specified amount of time and that have an instability severity equal to or greater than a specified instability severity threshold, wherein instability severity for a given instability event is determined as an amount that the minute ventilation ratio corresponding to the instability event is below the specified reference ratio; and plotting the determined periods of time on a P-IE graph, the P-IE graph having a first axis representing time and a second axis corresponding to P-IE values.

Example 18 includes subject matter relating to a computer readable storage medium comprising instructions, that when executed by one or more processors, carry out operations comprising: receiving raw sensor data from a monitoring device worn by a user during a monitoring session, the raw sensor data corresponding to girth measurements relating to a torso of the user; averaging the raw sensor data over specified periods of time to obtain averaged sensor samples; determining the beginning of each of a plurality of breath cycles and associating each beginning of a breath cycle with a corresponding timestamp, wherein the beginning of a breath cycle is determined when an averaged sensor sample increases from a preceding identified trough in the averaged sensor samples; determining the end of each the plurality of breath cycles and associating each end of a breath cycle with a corresponding timestamp, wherein the end of a given breath cycle is determined when an averaged sensor sample is at least one of (i) less than an averaged sensor sample corresponding to the beginning of the given breath cycle or (ii) less than a maximum averaged sensor sample corresponding to the given breath cycle by at least a specified value; for each breath cycle: determining a trough value of the breath cycle as corresponding to a lowest value of the raw sensor data between the timestamps associated with the beginning and end of the breath cycle, and associating the trough value with a corresponding timestamp; and determining a peak value of the breath cycle as corresponding to a highest value of the raw sensor data between the timestamps associated with the beginning and end of the breath cycle, and associating the peak value with a corresponding timestamp; and plotting each breath cycle on a vector graph as a breath vector, the vector graph having a first axis representing time and a second axis corresponding to breath volume, wherein for a given breath cycle, the starting point of the corresponding breath vector corresponds to the trough value of the given breath cycle and is plotted at a time corresponding to the timestamp associated with the trough value of the given breath cycle, and the end point of the corresponding breath vector corresponds to the peak value of the given breath cycle and is plotted at a time corresponding to the timestamp associated with the peak value of the given breath cycle.

In Example 19, the subject matter of Example 18 optionally includes wherein plotting each breath cycle on a vector graph as a breath vector further comprises connecting the end point of each breath vector with the starting point of an immediately subsequent breath vector, if there is one.

In Example 20, the subject matter of Example 18 or 19 optionally includes wherein the instructions carry out further operations comprising: receiving positional data from the monitoring device corresponding to the monitoring session; determining a predominant postural position of the user at various times during the monitoring session based on the positional data; and plotting the determined predominant postural positions on a posture graph, the posture graph having a first axis representing time and a second axis corresponding to postural position.

In Example 21, the subject matter of Example 20 optionally includes wherein: plotting each breath cycle on a vector graph as a breath vector comprises displaying the vector graph in a plurality of rows; and plotting the determined predominant postural positions on a posture graph comprises displaying the posture graph with its first axis substantially perpendicular to the first axis of the vector graph.

In Example 22, the subject matter of any of Examples 18 to 21 optionally includes wherein the instructions carry out further operations comprising: determining respiratory rate of the user at various times during the monitoring session; and plotting the respiratory rates on a respiratory rate graph, the respiratory rate graph having a first axis representing time and a second axis corresponding to respiratory rate.

In Example 23, the subject matter of Example 22 optionally includes wherein: plotting each breath cycle on a vector graph as a breath vector comprises displaying the vector graph in a plurality of rows; and plotting the respiratory rates on a respiratory rate graph comprises displaying the respiratory rate graph with its first axis substantially perpendicular to the first axis of the vector graph.

In Example 24, the subject matter of any of Examples 18 to 23 optionally includes wherein the instructions carry out further operations comprising determining a chaos index for each of one or more breath cycles, wherein determining a chaos index for a given breath cycle comprises: determining the length of a curve (Lraw) passing through the raw sensor data between the timestamps associated with the beginning and end of the given breath cycle; summing the length of the breath vector corresponding to the given breath cycle and the length of an exhalation vector that starts at the end point of the breath vector corresponding to the given breath cycle and ends at the starting point of the breath vector corresponding to an immediately subsequent breath cycle to determine a total vector length (Lvector); and determining the ratio of Lraw to Lvector.

ADDITIONAL NOTES

The above detailed description includes references to the accompanying drawings, which form a part of the detailed description. The drawings show, by way of illustration, specific embodiments that can be practiced. These embodiments may also be referred to herein as “examples.” Such embodiments or examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. That is, the above-described embodiments or examples or one or more aspects, features, or elements thereof can be used in combination with each other.

As used herein, the terms “substantially” or “generally” refer to the complete or nearly complete extent or degree of an action, characteristic, property, state, structure, item, or result. For example, an object that is “substantially” or “generally” enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of “substantially” or “generally” is equally applicable when used in a negative connotation to refer to the complete or near complete lack of an action, characteristic, property, state, structure, item, or result. For example, an element, combination, embodiment, or composition that is “substantially free of” or “generally free of” an element may still actually contain such element as long as there is generally no significant effect thereof.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

What is claimed is:

1. A non-transitory computer readable storage medium comprising instructions, that when executed by one or more processors, carry out operations comprising:

receiving raw sensor data from a monitoring device worn by a user during a monitoring session, the raw sensor data corresponding to girth measurements relating to a torso of the user;

averaging the raw sensor data over specified periods of time to obtain averaged sensor samples;

determining the beginning of each of a plurality of breath cycles and associating each beginning of a breath cycle with a corresponding timestamp, wherein the beginning of a breath cycle is determined when an averaged sensor sample increases from a preceding identified trough in the averaged sensor samples;

determining the end of each the plurality of breath cycles and associating each end of a breath cycle with a corresponding timestamp, wherein the end of a given breath cycle is determined when an averaged sensor sample is at least one of (i) less than an averaged sensor sample corresponding to the beginning of the given breath cycle or (ii) less than a maximum averaged sensor sample corresponding to the given breath cycle by at least a specified value;

for each breath cycle:

determining a trough value of the breath cycle as corresponding to a lowest value of the raw sensor data between the timestamps associated with the beginning and end of the breath cycle, and associating the trough value with a corresponding timestamp; and determining a peak value of the breath cycle as corresponding to a highest value of the raw sensor data between the timestamps associated with the beginning and end of the breath cycle, and associating the peak value with a corresponding timestamp;

plotting each breath cycle on a vector graph as a breath vector, the vector graph having a first axis representing time and a second axis corresponding to breath volume, wherein for a given breath cycle, the starting point of the corresponding breath vector corresponds to the trough value of the given breath cycle and is plotted at a time corresponding to the timestamp associated with the trough value of the given breath cycle, and the end point of the corresponding breath vector corresponds to the peak value of the given breath cycle and is plotted at a time corresponding to the timestamp associated with the peak value of the given breath cycle;

receiving positional data from the monitoring device corresponding to the monitoring session;

determining a predominant postural position of the user at various times during the monitoring session based on the positional data; and plotting the determined predominant postural positions on a posture graph, the posture graph having a first axis representing time and a second axis corresponding to postural position;

wherein:

plotting each breath cycle on a vector graph as a breath vector comprises displaying the vector graph in a plurality of rows, each row corresponding to a respective time period; and plotting the determined predominant postural positions on a posture graph comprises displaying the posture graph with its first axis substantially perpendicular to the first axis of the vector graph, and aligning the posture graph with the vector graph such that for each row of the vector graph, that row is aligned with a portion of the posture graph corresponding to the respective time period of that row.

2. The non-transitory computer readable storage medium of claim 1, wherein plotting each breath cycle on a vector graph as a breath vector further comprises connecting the end point of each breath vector with the starting point of an immediately subsequent breath vector, if there is one.

3. The non-transitory computer readable storage medium of claim 1, wherein the instructions carry out further operations comprising:

determining respiratory rate of the user at various times during the monitoring session; and plotting the respiratory rates on a respiratory rate graph, the respiratory rate graph having a first axis representing time and a second axis corresponding to respiratory rate.

4. The non-transitory computer readable storage medium of claim 3, wherein:

plotting the respiratory rates on a respiratory rate graph comprises displaying the respiratory rate graph with its first axis substantially perpendicular to the first axis of the vector graph.

5. A non-transitory computer readable storage medium comprising instructions, that when executed by one or more processors, carry out operations comprising:

receiving raw sensor data from a monitoring device worn by a user during a monitoring session, the raw sensor data corresponding to girth measurements relating to a torso of the user;

averaging the raw sensor data over specified periods of time to obtain averaged sensor samples;

determining the beginning of each of a plurality of breath cycles and associating each beginning of a breath cycle with a corresponding timestamp, wherein the beginning of a breath cycle is determined when an averaged sensor sample increases from a preceding identified trough in the averaged sensor samples;

determining the end of each the plurality of breath cycles and associating each end of a breath cycle with a corresponding timestamp, wherein the end of a given breath cycle is determined when an averaged sensor sample is at least one of (i) less than an averaged sensor sample corresponding to the beginning of the given breath cycle or (ii) less than a maximum averaged sensor sample corresponding to the given breath cycle by at least a specified value;

for each breath cycle:

determining a trough value of the breath cycle as corresponding to a lowest value of the raw sensor data between the timestamps associated with the beginning and end of the breath cycle, and associating the trough value with a corresponding timestamp; and determining a peak value of the breath cycle as corresponding to a highest value of the raw sensor data between the timestamps associated with the beginning and end of the breath cycle, and associating the peak value with a corresponding timestamp;

plotting each breath cycle on a vector graph as a breath vector, the vector graph having a first axis representing time and a second axis corresponding to breath volume, wherein for a given breath cycle, the starting point of the corresponding breath vector corresponds to the trough value of the given breath cycle and is plotted at a time corresponding to the timestamp associated with the trough value of the given breath cycle, and the end point of the corresponding breath vector corresponds to the peak value of the given breath cycle and is plotted at a time corresponding to the timestamp associated with the peak value of the given breath cycle; and determining a chaos index for each of one or more breath cycles, wherein determining a chaos index for a given breath cycle comprises:

determining the length of a curve (Lraw) passing through the raw sensor data between the timestamps associated with the beginning and end of the given breath cycle;

summing the length of the breath vector corresponding to the given breath cycle and the length of an exhalation vector that starts at the end point of the breath vector corresponding to the given breath cycle and ends at the starting point of the breath vector corresponding to an immediately subsequent breath cycle to determine a total vector length (Lvector); and determining the ratio of Lraw to Lvector.

6. The non-transitory computer readable storage medium of claim 5, wherein plotting each breath cycle on a vector graph as a breath vector further comprises connecting the end point of each breath vector with the starting point of an immediately subsequent breath vector, if there is one.

7. The non-transitory computer readable storage medium of claim 5, wherein the instructions carry out further operations comprising:

receiving positional data from the monitoring device corresponding to the monitoring session;

determining a predominant postural position of the user at various times during the monitoring session based on the positional data; and plotting the determined predominant postural positions on a posture graph, the posture graph having a first axis representing time and a second axis corresponding to postural position.

8. The non-transitory computer readable storage medium of claim 7, wherein:

plotting each breath cycle on a vector graph as a breath vector comprises displaying the vector graph in a plurality of rows; and plotting the determined predominant postural positions on a posture graph comprises displaying the posture graph with its first axis substantially perpendicular to the first axis of the vector graph.

9. The non-transitory computer readable storage medium of claim 5, wherein the instructions carry out further operations comprising:

determining respiratory rate of the user at various times during the monitoring session; and plotting the respiratory rates on a respiratory rate graph, the respiratory rate graph having a first axis representing time and a second axis corresponding to respiratory rate.

10. The non-transitory computer readable storage medium of claim 9, wherein:

plotting each breath cycle on a vector graph as a breath vector comprises displaying the vector graph in a plurality of rows; and plotting the respiratory rates on a respiratory rate graph comprises displaying the respiratory rate graph with its first axis substantially perpendicular to the first axis of the vector graph.

11. A non-transitory computer readable storage medium comprising instructions, that when executed by one or more processors, carry out operations comprising:

receiving raw sensor data from a monitoring device worn by a user during a monitoring session, the raw sensor data corresponding to girth measurements relating to a torso of the user;

averaging the raw sensor data over specified periods of time to obtain averaged sensor samples;

determining the beginning of each of a plurality of breath cycles and associating each beginning of a breath cycle with a corresponding timestamp, wherein the beginning of a breath cycle is determined when an averaged sensor sample increases from a preceding identified trough in the averaged sensor samples;

determining the end of each the plurality of breath cycles and associating each end of a breath cycle with a corresponding timestamp, wherein the end of a given breath cycle is determined when an averaged sensor sample is at least one of (i) less than an averaged sensor sample corresponding to the beginning of the given breath cycle or (ii) less than a maximum averaged sensor sample corresponding to the given breath cycle by at least a specified value;

for each breath cycle:

determining a trough value of the breath cycle as corresponding to a lowest value of the raw sensor data between the timestamps associated with the beginning and end of the breath cycle, and associating the trough value with a corresponding timestamp; and determining a peak value of the breath cycle as corresponding to a highest value of the raw sensor data between the timestamps associated with the beginning and end of the breath cycle, and associating the peak value with a corresponding timestamp;

plotting each breath cycle on a vector graph as a breath vector, the vector graph having a first axis representing time and a second axis corresponding to breath volume, wherein for a given breath cycle, the starting point of the corresponding breath vector corresponds to the trough value of the given breath cycle and is plotted at a time corresponding to the timestamp associated with the trough value of the given breath cycle, and the end point of the corresponding breath vector corresponds to the peak value of the given breath cycle and is plotted at a time corresponding to the timestamp associated with the peak value of the given breath cycle;

determining respiratory rate of the user at various times during the monitoring session; and plotting the respiratory rates on a respiratory rate graph, the respiratory rate graph having a first axis representing time and a second axis corresponding to respiratory rate wherein:

plotting each breath cycle on a vector graph as a breath vector comprises displaying the vector graph in a plurality of rows, each row corresponding to a respective time period; and plotting the respiratory rates on a respiratory rate graph comprises displaying the respiratory rate graph with its first axis substantially perpendicular to the first axis of the vector graph, and aligning the respiratory rate graph with the vector graph such that for each row of the vector graph, that row is aligned with a portion of the respiratory rate graph corresponding to the respective time period of that row.

12. The non-transitory computer readable storage medium of claim 11, wherein plotting each breath cycle on a vector graph as a breath vector further comprises connecting the end point of each breath vector with the starting point of an immediately subsequent breath vector, if there is one.

13. The non-transitory computer readable storage medium of claim 11, wherein the instructions carry out further operations comprising:

receiving positional data from the monitoring device corresponding to the monitoring session;

determining a predominant postural position of the user at various times during the monitoring session based on the positional data; and plotting the determined predominant postural positions on a posture graph, the posture graph having a first axis representing time and a second axis corresponding to postural position.

14. The non-transitory computer readable storage medium of claim 13, wherein:

plotting the determined predominant postural positions on a posture graph comprises displaying the posture graph with its first axis substantially perpendicular to the first axis of the vector graph.

* * * * *